United States Patent [19]
Vijg et al.

[11] Patent Number: 6,007,231
[45] Date of Patent: Dec. 28, 1999

[54] METHOD OF COMPUTER AIDED AUTOMATED DIAGNOSTIC DNA TEST DESIGN, AND APPARATUS THEREFOR

[75] Inventors: Jan Vijg; Robert Bishop, both of Newton, Mass.

[73] Assignee: Academy of Applied Science, Concord, N.H.

[21] Appl. No.: 08/696,497

[22] Filed: Aug. 14, 1996

[51] Int. Cl.[6] .......................... G06F 17/00; G01N 31/00; C12P 19/34; C07H 21/04

[52] U.S. Cl. .......................... 364/497; 364/496; 364/499; 435/91.1; 435/91.2; 536/24.33

[58] Field of Search ..................... 364/497, 496, 364/499; 435/91.1, 91.2, 174; 204/182.8; 536/23.1, 24.3, 24.33

[56] References Cited

PUBLICATIONS

Abrams et al. Genes, Chromosomes & Cancer 6: 73–85, 1993.
Lerman et al. methods in Enzymology 155: 483–501, 1987.
Li and Vijg, Nucleic Acids Research 24: 538–539, 1996.
State Street Bank and Trust Co. v. Signature Financial Group Inc. (DC MAss) 38 USPQ2d 1530, 1996.
In re Allapat 31 USPQ 1545 ( CAFC , 1994.
In re Shrader 30 USPQ2d 1445 ( CAFC), 1994.
Arrythmia Research Technology Inc. v. Corazonix 22 USPQ 1033, 1992.
Diamond v Diehr 209 USPQ 2d (U.S. Supreme Ct), 1981.
In re Gelnovatch 201 USPQ 136 (CCPA), 1979.
In re Walter 205 USPQ 397 (CCPA), 1980.

*Primary Examiner*—Kenneth R. Horlick
*Assistant Examiner*—Jeffrey Siew
*Attorney, Agent, or Firm*—Rines and Rines

[57] ABSTRACT

The invention encompasses a semi-automatic and/or automatic computer-aided technique for designing comprehensive DNA diagnostic tests for mutations in disease genes through searching for optimized conditions for PCR amplification and for optimal melting behavior in denaturing gradient gels and for optimal distribution in two-dimensional electrophoresis display of the mutational target fragments.

27 Claims, 17 Drawing Sheets

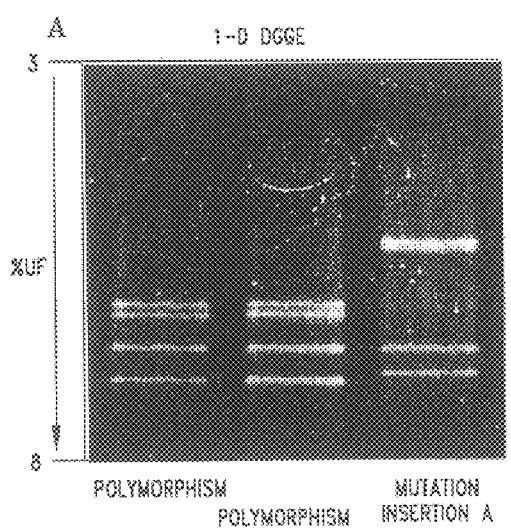
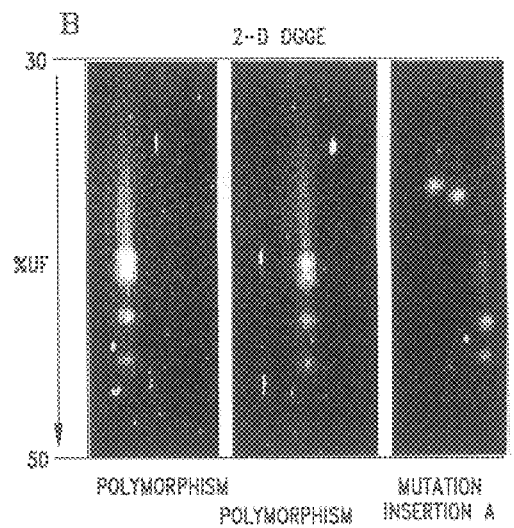
FIG. 2A
FIG. 2B

METHOD OF COMPUTER AIDED AUTOMATED DIAGNOSTIC DNA TEST DESIGN, AND APPARATUS THEREFOR

The present invention relates to techniques for designing comprehensive DNA diagnostic tests for mutations in disease genes, being more particularly directed to computer-aided searching for optimized predicted conditions for Polymerase Chain Reaction (PCR) amplification, including multiplex PCR amplification, optimal melting behavior in denaturing gradient gels and optimal distribution by two-dimensional electrophoresis of the mutational target fragments, thereby to provide an overall design for actual diagnostic tests.

BACKGROUND OF THE INVENTION

As is well-known, a strand of DNA is comprised of four different nucleotides, as determined by their bases: Adenine, Thymine, Cytosine and Guanine, respectively designated A, T, C, G. For each strand of DNA, there is a homologous strand in which A pairs with T, and C pairs with G. A specific sequence of bases which codes for a protein is referred to as a gene, and that gene is segmented into regions which are responsible for protein compositions (exons) and regions which do not contribute to protein composition (introns). An exon can vary in length from about 30 basepairs to thousands of basepairs (bp). For purposes of the present invention, however, primary concern resides with the coding regions of the gene(exons), though the test procedures of the invention can be easily appropriately modified, where desired, to screen for carcinogenic mutations in the introns, also, and for other purposes as well.

DNA diagnostic testing of genes with mutational defects is important for ascertaining information with regard to individual susceptibility to particular diseases, classification of the disease in a therapeutically relevant sub-group, the carriership (and potential transfer) or prenatal presence of birth defects, and other important purposes. The gold standard in DNA diagnostic testing for the presence of mutations is DNA sequencing, which involves the complete decoding of the gene. This, however, is time-consuming and inefficient. Time-consuming because despite numerous ongoing attempts to simplify and greatly accelerate the process, all currently used routine sequencing systems are still based on the principle originally developed by Sanger and colleagues (as described, for example, in *Molecular Pathology*, Heim and Silverman, 1990, pages 7–10), and only partially automated. They are inefficient because, instead of simply determining differences between entire DNA fragments, every DNA fragment must be completely decoded before any differences from normal (mutations) are revealed. The fact that the exact location of a disease-causing mutation can be different from one individual to the next, moreover, precludes the possibility of only testing for frequently occurring known mutations. Indeed, the many different mutations that may convert a healthy gene into a diseased gene makes it necessary in each case to inspect the entire gene at all possible positions for mutations (termed gene scanning) rather than for only a few frequently occurring ones (mutation screening). Mutation screening methods are relatively simple and cost-efficient. Outside DNA sequencing, potential gene scanning systems are scarce and their cost-efficiency is questionable.

Recently, a method was disclosed by one of the applicants of the present patent application for comparative scanning of 100–600 basepairs (bp) gene fragments by multiplex PCR amplification followed by two-dimensional electrophoretic separation in polyacrylamide gels on the basis of both size and basepair sequence; "Multiplex Co-amplification of 24 Retinoblastoma Gene Exons After Pre-amplification By Long-Distance PCR," Jan Vijg and Daizong Li, *Nucleric Acids Research*, 1996, Vol. 24, No. 1, p. 538-9. "Two-Dimensional DNA Typing", Jan Vijg, *Molecular Biotechnology*, pages 275, on, Vol. 4, 1995; and in copending U.S. patent application Ser. No. 08/471,249, filed Jun. 6, 1995 for Method Of And Apparatus For Diagnostic DNA Testing now U.S. Pat. No. 5,814,49, issued Sep. 29, 1998. The latter can be accomplished by denaturing gradient gel electrophoresis (DGGE). This multiplexing technique for analyzing predetermined gene exons derived from DNA, involves adding primer pairs surrounding successive groups of the gene exons followed by effecting long-distance PCR amplifications thereof in a common tube or vessel (multiplex long-PCR) to achieve relatively long resulting amplicons; adding further primer pairs surrounding each of the gene exons or parts thereof, and then effecting multiplex PCR amplifications thereof in the common tube or vessel with relatively short resulting amplicons; and electrophoretically separating the gene fragments. By size separation, mutations representing deletions or insertions varying from several to many basepairs can be detected. In DGGE, point mutations, such as basepair substitutions are also detectable. This is due to the tendency of double-stranded DNA fragments to melt at a point in the gradient where the temperature equals the melting temperature of the lowest-meiting domain of the fragment.

In the process of PCR amplification, the mutational target fragments (e.g., gene exons) are surrounded by primers, i.e., short (about 20 base pairs) single-stranded DNA fragments. Primers are chosen in such a way that they are complementary (bind to) positions at the left and right boundaries or ends of the target fragments. By using appropriate enzymes that extend each primer inwards, towards each other, the mutational target can be copied. This can be repeated a great number of times in a so-called thermocycler—a machine that first heats up the DNA sample, thereby separating the single strands followed by cooling down, which results in annealing of the primers to their target sequences, and the subsequent enzymatic extensions of the primers by polymerase enzymes. The net result is an amplification of the fragment in between the primers of typically one million times. This provides enough target DNA to detect the fragment by using a DNA-binding dye, after electrophoretic separation, without the use of radioactive tracers; the rest of the DNA being now a relatively small amount and invisible.

The positioning of the primers is critical because, for such short sequences, there is ample opportunity to bind elsewhere in the complex DNA molecules that form the starting material of the test. This would lead to the copying of other fragments than the ones of interest. Positioning of primers is even more critical in denaturing gradient gel electrophoresis, where each fragment must have an optimal melting temperature in order to allow all possible mutations to be detected. It is common practice to couple one of the two primers surrounding a gene target fragment to a GC-rich clamp sequence of about 30 basespairs long. This clamp is very stable and functions as the highest melting domain; that is, the part of the DNA molecule that keeps the fragment together. This is important because once a fragment migrates off the gel it can no longer be detected. In PCR-DGGE it is just as important, furthermore, that the target fragment consists of one single domain (flat throughout the gene fragment) that has a lower stability than the GC-clamp. In that case, it will melt earlier than the clamp, resulting in a structure that is partially double-stranded (the clamp) and partially single-stranded (the target fragment): a so-called branched structure. Such a fragment will be greatly retarded in the gel. Typically, the exact position where such a fragment melts (and thus halts its migration) is completely dependent on its sequence. With a fragment of, say, 500 basepairs, one single basepair difference will lead to a migrational difference that can be employed by detecting mutations in such fragments as a migrational difference with a control (wildtype) fragment. Hence, in contrast to DNA sequencing, DGGE does allow comparative scanning of whole fragments for mutational differences without the need to completely decode each molecule.

To carry out DGGE in two dimensions (2-D) rather than in one, increases the efficiency of the system as well as its reliability. Indeed, in a 2-D gel, many more fragments can be analyzed simultaneously than by a 1-D separation. It is more reliable because every fragment can be defined by both its melting temperature and its size. A disadvantage, however, resides in its increased complexity, requiring extreme attention to the design of the test. Since the design of a DGGE test itself is not trivial (primers must be chosen in a way that the amplified fragments represent a single domain, as before discussed), the 2-D principle adds a dimension in complexity as well as in resolution. A typical design of PCR primers, moreover, must take into consideration many other variables inherent to the PCR process, such as primer annealing temperatures.

As disclosed in the above-cited Vijg papers and the said patent application, the two-step PCR process enables many different exons to be amplified simultaneously in the same reaction. In this method, first, groups of target fragments (e.g., groups of exons) are amplified as large 5–40 kb amplicons, for example, by long-distance PCR (an improved form of PCR in which more efficient polymerase enzymes are employed that generate longer fragments). Second, with these amplicons as templates, large numbers of individual target sequences can now be amplified simultaneously in the same reaction vessel under a single set of experimental conditions. Normally it is very difficult to find one set of reaction conditions under which multiple fragments specified by multiple primer pairs are amplified simultaneously (i.e., multiplex PCR). Probably because the pre-amplification by long-distance PCR increases the amount of target sequences relative to the rest of the complex genomic DNA, flexibility with respect to the subsequent PCR amplification of the target sequences is much greater than normal, which permits extensive multiplexing; i.e., co-amplification of different target fragments in the same reaction.

This method of extensive multiplexing greatly economized the process of template preparation in genetic testing over earlier techniques for inspecting for mutations after PCR amplifying the many distributed exons of the often very large disease genes. As an example, it is now possible, to generate a collection of as many as 25 fragments corresponding to 26 exons of the tumor suppresser gene RB1 in one single two-step PCR reaction. After the two-step multiplex PCR amplification, a single 2-dimensional electrophoretic separation, as the third step, is sufficient to resolve all these fragments and detect all possible mutations as variations in fragment spot position. With this system, a genetic testing method has become available that is both highly accurate (in detecting all possible mutations) and cost-efficient.

The only remaining drawback involves the absence of a rapid design of an optimal test for one or more individual genes involved in a particular disease. The human genome, indeed, contains an estimated number of 100,000 different genes, many of which might ultimately prove to be involved in one or more diseases. To design a set of PCR primers for many different genes and/or gene combinations that fulfill criteria for optimal (multiplex) PCR, optimal denaturing gradient electrophoretic separation and 2-D distribution is not trivial. As shown in later-described FIG. 1, the computer-assisted test design of the invention must provide, for an optimal 2-D genetic test for one or multiple genes with predicted primer and GC-clamp respective positions and lengths for meeting optimal melting criteria, PCR criteria and 2-D spot distribution criteria.

The present invention is directed to solving this problem and, through a computer-assisted procedure, to semi-automatically and/or automatically design multiplex PCR/2-D electrophorctic tests for one or more genes.

OBJECTS OF INVENTION

An object of the invention, accordingly, is to provide a new and improved method of and apparatus for computer-aided rapid design of a genetic test based on multiplex PCR amplification of the target sequences, followed by electrophoretic separation of the fragment mixture in two dimensions: size and basepair sequence.

A further object is to provide for superior performance of multiplex PCR/2-D electrophoresis tests through the heretofore unavailable rapidity in computer software-aided selecting of optimal sets of conditions among the large number of possibilities available.

Other and further objects will be described hereinafter and are more particularly delineated in the appended claims.

DESCRIPTION OF THE DRAWINGS

The invention will now be described in connection with the accompanying drawings in which:

FIGS. 2A and 2B represent experimentally electrophoretically obtained mutation displays of exemplary 1-D (FIG. 2A) and 2-D (FIG. 2B) DGGE tests on illustrative BRCA-1 gene fragments;

SUMMARY OF THE INVENTION

Figure 1:
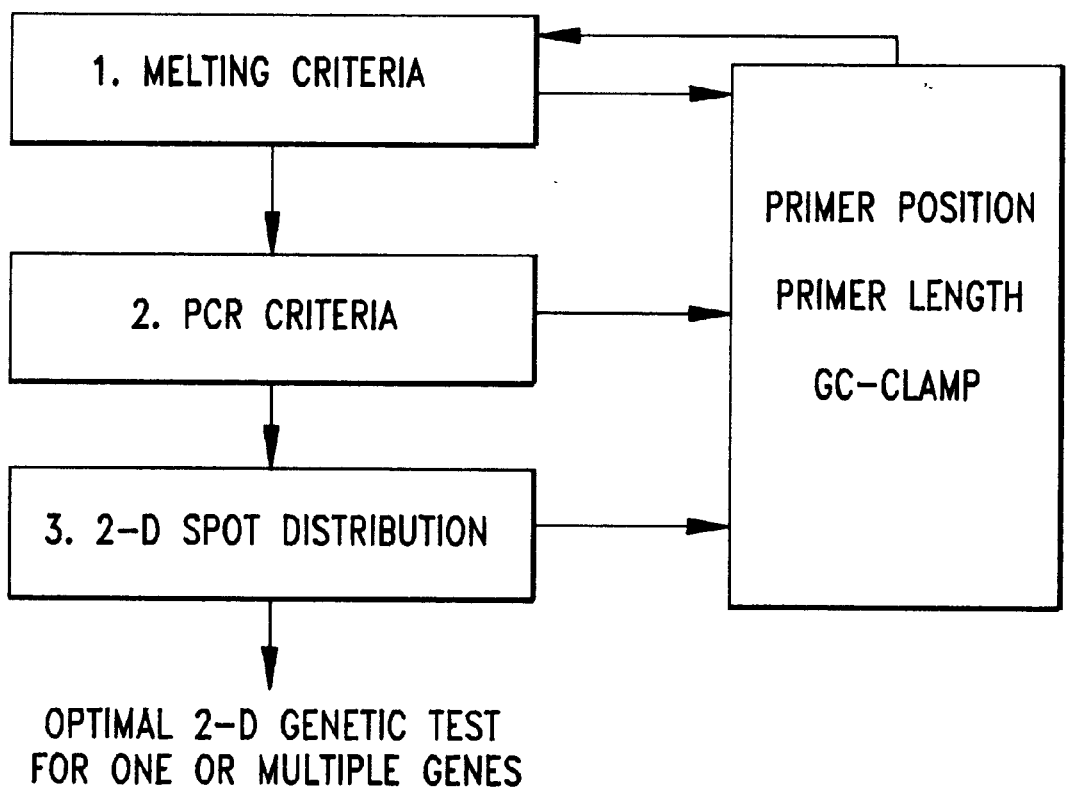
FIG. 1, as earlier mentioned, is a block diagram of the underlying computer-assisted system for optimal 2-D genetic test design for one or multiple genes.

In summary, the invention embraces a method of computer-aided genetic test design that involves capture of a gene sequence file, e.g., from Genbank; indicating the start and ends of desired target sequences, generating optimal melting profiles, PCR conditions and 2-D distributions by varying (1) fragment size (gap-size), (2) GC-clamp, and (3) primer size; and reporting the selected optimal primer sets for being synthesized.

From a more detailed viewpoint, the invention embraces a computer-assisted method for generating the design of optimized and comprehensive genetic DNA diagnostic tests based on PCR/2-D electrophoresis for screening mutations in genes, that comprises, inputting a computer microprocessor with a desired gene exon fragment ATGC letter sequence; programming and controlling the microprocessor first to select a trial start and end of the sequence; then, selecting and positioning trial primer letter pairs to define the opposite boundaries of the exons to be tested; adding a trial GC clamp to at least one primer; generating trial melting profiles for the trial primers and GC clamp to determine whether the profile consists of a relatively high-melting GC clamp peak and a substantially single flat domain of relatively low-melting value for the fragments; in the event that the trial profile has multiple and not a satisfactory single flat domain, changing one or both of other trial primer sequences and GC clamp sizes and generating said profiles therefrom until such a satisfactory single flat domain is attained, and for primers of each pair having substantially similar annealing temperatures suitable for PCR annealing; comparing the primer letter sequence with other known gene sequences in the context of the total letter sequence of the gene exon to insure the uniqueness of the sequences and to avoid overlap with any other than the selected gene fragment; simulating a 2-D distribution of the fragments defined by the primer pairs by separation along one dimension by size and along an orthogonal dimension by melting temperature of the fragment; selecting a gradient of increasing melting temperatures along the orthogonal dimension to allow an optimal spread of the fragments therealong; and reporting the selected primer sets and temperature gradient, thereby providing an optimal design for an actual PCR/2-D electrophoresis test.

Preferred and best mode designs and details are hereinafter fully described.

DESCRIPTION OF PREFERRED EMBODIMENTS

The present invention, as before stated, involves a procedure for the semi-automated and/or automated computer-aided design of optimized genetic screening tests based on PCR/2-D electrophoresis, and preferably multiplex PCR/2-D electrophoecsis.

Brief Summary Of Preferred Diagnostic Procedural Techniques

In accordance with the procedures useful also with the computer-assisted semi-automated and automatic features of the invention, two DNA fragments of, for example, 11–50 kb are constructed which are homologous to an 18 to 25 base sequence in the intronic sequence both preceding and following an exon; the leading and trailing primers. Because many mutations occur in the transition from intron to exon, these priming sites, as before explained, are separated from the exon by a gap of at least, say, 10 base pairs, and usually not more than about 40 base pairs. For each "multiplex" test herein described, optimal primers for all of the fragments would have comparable annealing temperatures, as previously noted. If the primers all anneal within a few degrees centigrade of one another, each fragment should be equally amplified in the multiplex PCR.

Once primers are selected, the exon is amplified from template DNA by PCR. The DNA sequence which is amplified was earlier referred to as a PCR fragment or an amplicon, including the exon, the primer sequences, the intronic gaps between the exon and primer sequences, as well as usually a 30–60 base pair GC clamp, for example, which will be discussed later in reference to the computer software programming of the present invention. With such operation, the PCR fragment is at least about 86 base pairs longer than the exon itself. Following a successful multiplex PCR, millions of copies of the desired fragments exist. These can be viewed on a gel following electrophoresis on both size and denaturing gradient gels; it being important that each amplicon has its own unique spot on the 2-Dimensional mapping. In other words, the fragment should have a size and melting temperature unique to all other fragments included in the same test. The computer software of the invention, accordingly, is designed, as later detailed, to enable the user more readily to attain a test in which these criteria are optimally met.

With regard generally to the software design for achieving the purposes of the invention, an optimal test design would insure that each fragment would have a different size as well as a different Tm or melting temperature. Using the later-described program, the fragment length can be varied by adjusting the length of the primer and by adjusting the position of the primer. Primer length for short PCR, as before described, generally ranges from about 18–25 bases pairs, and primer position is usually between about 10 and 30 base pairs from the beginning and end of the exon. This is also described as the before-mentioned gap of, say, 10–30 bp.

To determine the Tm of the fragment, the computer uses the Lerman Program (described, for example, in "Computational Simulation of DNA Melting and Its Application to Denaturing gradient gel Electrophoresis," Leonard S. Lerman and Silverstein, *Methods In Enzymology*, pages 482–501, Vol. 155, 1987), which will produce a theoretical Tm for a fragment. % UF (urea-formamide) is a chemical gradient from which the actual melting temperature Tm in degrees C. can be determined. Tm, moreover, is completely dependent upon base sequence. An A-T bond is less stable than a C-G bond. If a fragment has a high C-G content, therefore, it will melt lower in the gel (high Tm). Likewise, a fragment with a high A-T content will have a lower melting temperature and will melt sooner (lower % UF) in the gel. Because the bases have an effect on neighboring bases, a single mutation, called a point mutation, can alter the Tm of the entire fragment enough that it can be detected by denaturing gradient gel electrophoresis. For example, a point mutation in which a single T is changed to a G, is enough to change the melting temperature of the entire fragment from, for example, say 56% UF to 58% UF. If an A or a T changes to a C or a G, the mutant will have a higher Tm than the later-described healthy wild-type, due to the increased stability of the C-G bond. By similar reasoning, if a C or a G is mutated to an A or a T, the mutant will melt at a lower % UF to To.

At the end of the PCR, a special cycle is introduced in which the DNA is denatured and then allowed to bond with a complementary strand. Because every individual possesses two double stranded alleles or copies of the same gene, one from the mother and one from the father, four combinations of alleles can occur during this cycle. If a mutation is present in one of the alleles, it is referred to as the mutant strand. The four possible combinations would then be wild-type with wild-type, mutant with mutant, (these two are referred to as homoduplexes) and wild-type with mutant and mutant with wild-type (referred to as heteroduplexes).

Using the terminology mother (M) for the maternal allele and father (F) for the paternal allele, the four strands can be called MM and FF for the homoduplexes, and MF and FM for the heteroduplexes. When a mutation is present, the heteroduplexes will be notably less stable than either of the homoduplexes. If, for example, a point mutation from a T to a G has occurred, as above described, in the heteroduplex strands, there will be a destabilizing mismatch of A with C and T with G. The mismatch will cause the heteroduplexes to become far less stable than either of the homoduplexes. The presence of a mutant allele will accordingly produce four spots in a 2-D pattern. The mutant and wild-type homoduplexes are separated due to the nature of the mutation, and the two heteroduplexes will melt considerably higher in the gel due to their destabilizing mismatch. In the above example of a T to G point mutation, the wildtype homoduplex will melt at say, the before-mentioned 56% UF, the mutant homoduplex will melt at 58% UF, and the two heteroduplexes will melt considerably above, but at melting points different from each other.

Thus, in the example of a BRCA-1 mutation/heteroduplex shown in FIG. 2, two control samples with the same polymorphism and a sample with a 1-bp insertion mutation detected by 1-D DGGE (photographs A to the left)and by 2-D DGGE (photographs B to the right) illustrate how mutations are revealed in the system by the appearance of four bands an d spots, respectively, instead of one, and also show how the mutations or polymorphisms can b e clearly distinguished from one another.

In accordance with the present invention, the computer helps determine a test in which each fragment produces a distinct spot on the 2-D pattern in which a heteroduplex at that position can be easily detected.

Figure 3:
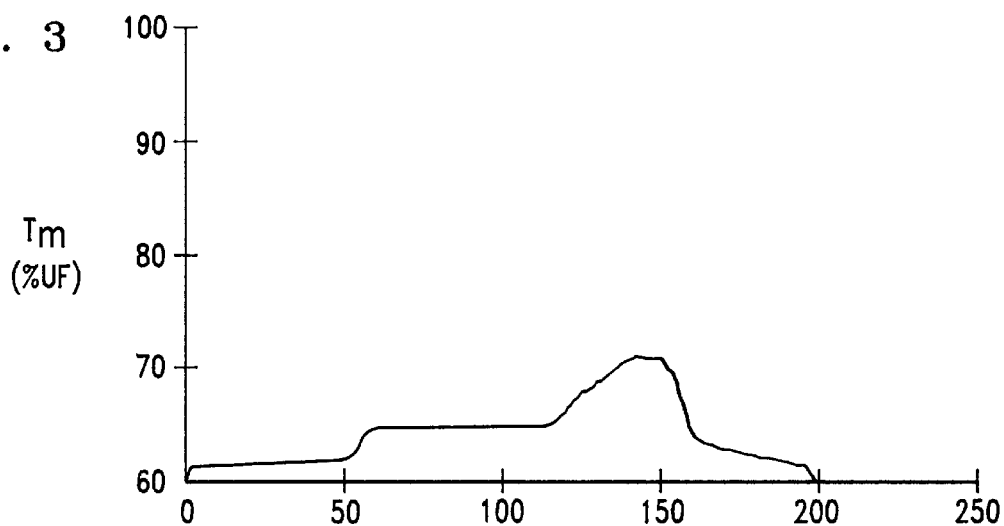
FIGS. 3, 4 and 5 are melting graphs (melting temperature vs. basepair offset) respectively of unacceptable multiple domain (FIG. 3) and acceptable left end (FIG. 4) and right end (FIG. 5) GC-clamped single domain profiles, taken for an exemplary retinoblastoma gene RB Exon 21, Fragment #1.
Figure 4:
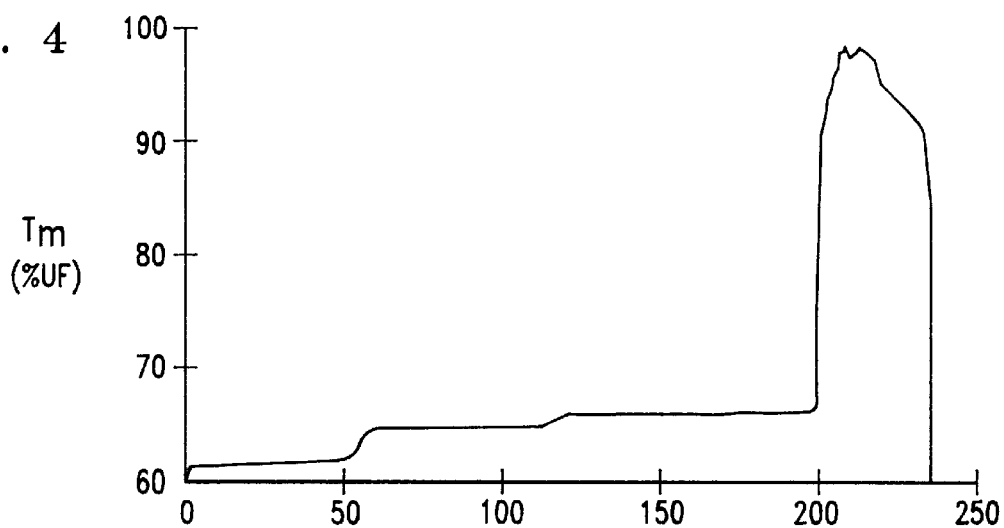
Figure 5:
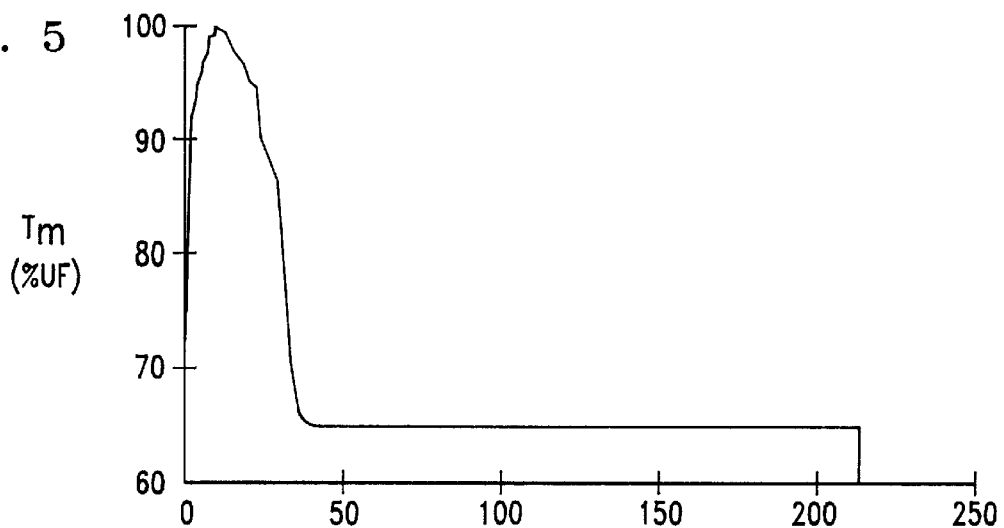

The earlier mentioned Lerman's Program ("Melt 87") calcula tes the melting temperature of each base pair. Then a program "SlideWrite" (described in the Advanced Graphics Software, Inc. Manual "SlideWrite® Plus for Windows™," 1994) is used to construct a melting graph in which the different melting domains of the fragment can easily be viewed. The generation of a CG clamp at one end of the fragment can influence the remainder of the strand to act as a single melting domain. Without such clamp, there are generally varying or multiple levels or domains for the fragment (FIG. 3). In the gel, a fragment with a GC clamp-induced single melting domain will melt, but the GC clamp itself, which melts considerably higher, will remain intact, as shown by the left-hand spike or peak in FIG. 4. Without a GC clamp, the fragment will simply split into two single strands and run off the gel. With the intact GC clamp, one strand enters a pore in the gel and the other enters another pore in the gel, and the intact GC clamp inhibits the fragment from moving any further in the gel. On the computer, a GC clamp of, for example, 30, 35 or 38 bp can be selected. The user can also choose to which primer the clamp should be added; FIG. 5 showing the clamp spike or peak to the right. The optimal melting pattern for a given fragment is arrived at through trial and error by selecting different primer lengths and positions and then trying different types and positions of GC clamp.

Operation Before The Present Invention

Before the present invention, the user would enter the DNA sequence. Then Lerman's program would begin asking questions. After the user had answered all the questions, the computer would calculate the melting temperature. After the melting temperature was arrived at, the outcome had to be transferred to another program which would construct a melting map of the fragment. If the fragment was not optimal, the user would return to the Lerman Program and alter the primer position/length manually, and determine where they had been placed on the first run. Once the user had achieved adequate melting maps for each of the fragments, a 2-D pattern could be constructed. If each spot did not have a unique position on the 2-D pattern, the user would have to start all over with whichever fragments overlapped.

Using this system, it took about four weeks to design a test for RB1, though still sub-optimal. With the program of the invention, a more optimal test was designed in about four hours. For more genes participating in the same test, design problems using MELT 87 became increasingly severe. The point comes at about 30 fragments when it is no longer possible to design manually according to the Lerman program.

Figure 15:
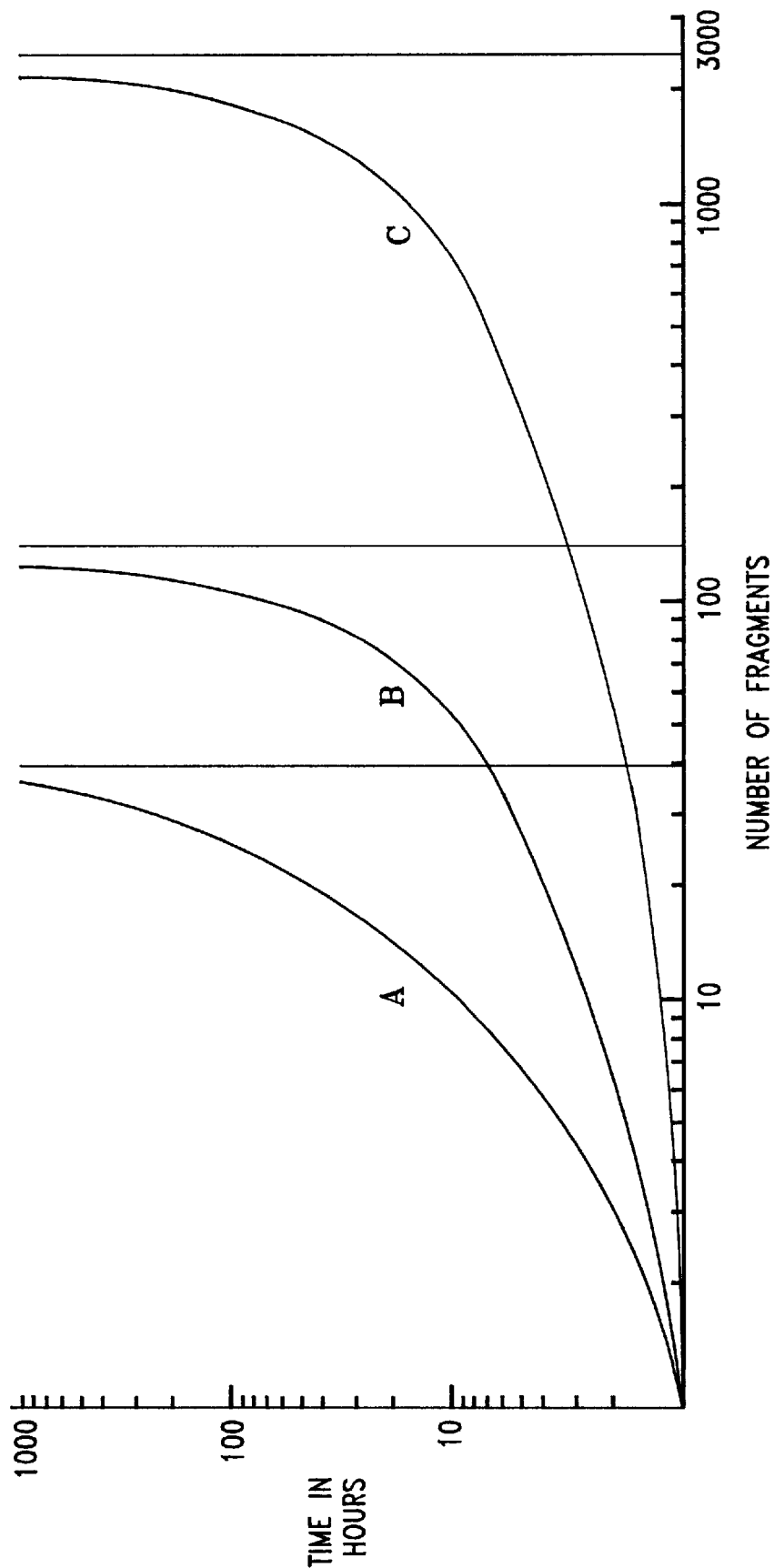
FIG. 15 is a time graph for test design for gene RB1 comparing the prior manual procedures with those of the invention.

FIG. 15 plots the time in hours as a function of number of fragments for test design for RBl of prior techniques and those of the invention.

Curve A depicts data taken during the construction of the two-dimensional DGGE test for RBl with fully manual software. 160 man hours were necessary to design a test which could adequately test the 27 exons of the retinoblastoma gene. Manual test design has an empirically determined capacity limit of about 40 fragments. Curve B, on the other hand, exhibits the drastic improvement in both time efficiency and test capacity experiences with semi-automated test design of the invention. With such semi-automated test design, the 27 exon RBl test was redesigned in approximately two and a half hours. Curve C, furthermore, predicts the exponential improvement fully automated test design software of the invention can have on the construction of two-dimensional multiplex tests, extending the capacity of two-dimensional multiplex gene testing even to the theoretical resolution limit of 2200 fragments on a 15 cm×15 cm denaturing gradient gel.

The program of the invention, furthermore, is able to calculate the Tm or annealing temperatures of the primers which also greatly facilitates the development of a megaplex PCR. In the past, the user had to consult yet another program for this information. Lastly, the program herein also searches the gene sequence to insure that each primer sequence is unique so that only the desired PCR fragment will be amplified. For this purpose, only the long-PCR fragments have to be searched through. Before this feature, the user would have to conduct a time-consuming blast search on the Internet in order to insure the uniqueness of the primers.

Figure 6A:
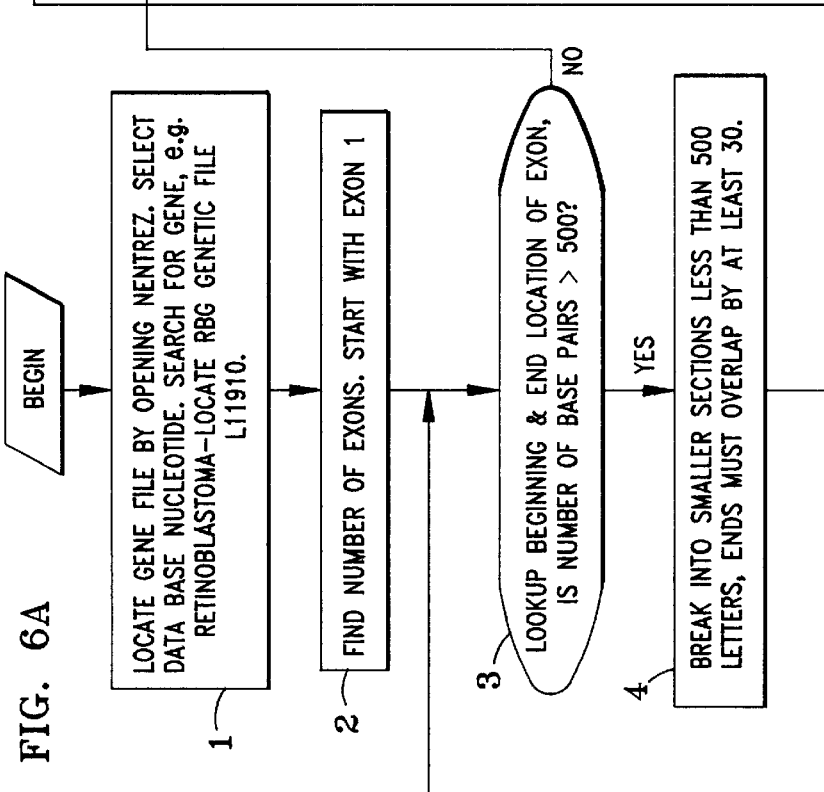
FIGS. 6A and 6B present flow diagrams of the present-day sequence of process steps required for determining appropriate primers and GC clamps for electrophoretic testing of designated gene fragments.
Figure 6B:
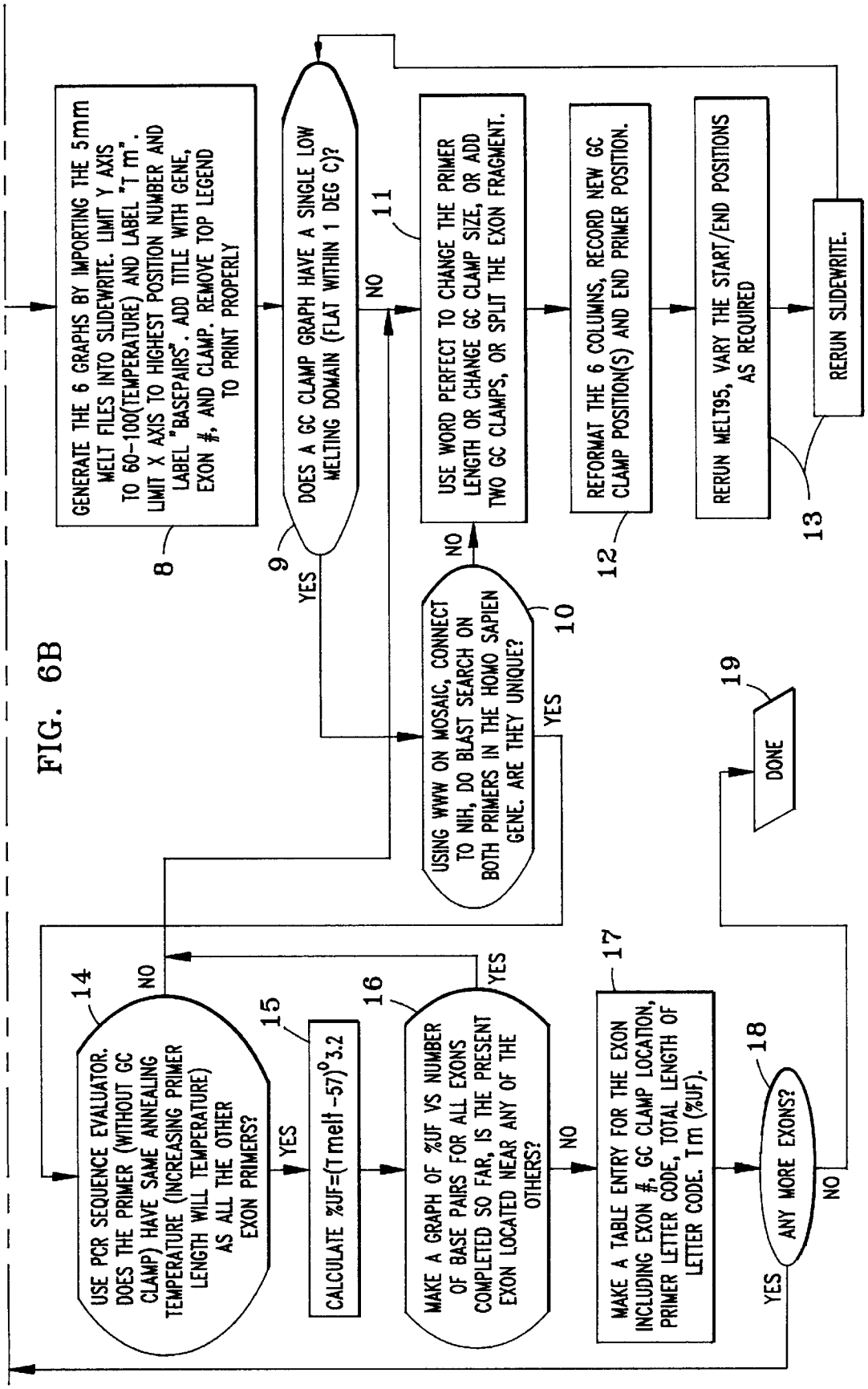

A typical series of these earlier time-consuming steps for finding appropriate primers, GC clamps, etc., and melting profiles, is presented in the Flow Charts of FIGS. 6A and 6B in connection with the illustrative case of retinoblastoma genes (RBG), selected as at 1, FIG. 6A. After finding the number of exons and starting with the first (2), the beginning and end locations of the exon are sought (3). If the number of base pairs is not greater than, for example, 500 letters (ATGC), the exon string is increased by at least, for example, 18 on each end, to create primers (5); but if there are more than 500 basepairs, they are broken up into smaller sections, with overlap as at (4). GC clamp sequences are added on the header and trailer (6) with stripping and reordering to leave 6 groups of separated ATCG sequences, and with a new exon file. Melting profiles are then run six times, three with three types of GC clamps on the leading primer and three on the trailing primer, at (7); and then corresponding graph profiles are generated at (8), FIG. 6B, such as are shown in FIGS. 4 and 5. If the melting profile for those primer sequences produces a satisfactory flat single domain at (9), as in FIGS. 4 and 5, using a search of the world wide web (www), uniqueness is determined at (10). If an unsatisfactory multiple or other unsatisfactory domain profile is obtained, however, as in FIG. 3, the primer sequence length and/or GC clamp size (or an added GC clamp) are varied, or the splitting of the exon fragment (11). The latter variations are also performed (11) if lack of uniqueness amongst the data base is found at (10). This is then followed by reformatting (12), recording new GC clamp positions, etc., and rerunning the melting profiles with variation of start/end positions, etc., as required (13). A determination of substantially the same annealing temperature for the primers, as required for PCR sequencing, is then made (14), with variations as at (11) effected if the primer temperatures are not substantially matched. The melting temperatures are then calculated from the percentages of urea formamide by the formula (15), enabling the making of a melting temperature versus number of basepairs for all exons complete (16). Should the present exon of interest be located too near any of the others, the variations of step (11) are employed to provide greater separation. If, however, there is no crowding, a table entry for the exon, including its number, GC clamp location, primer letter code and total length of letter code, and melting temperatures Tm are all recorded (17).

If there are more exons (18), the beginning step 3, FIG. 6A, and subsequent steps are repeated; otherwise, the procedure for exon primer determination is completed (19).

Operation in Accordance With The Invention

The computer-aided software-controlled microprocessor programming that underlies the semi-automatic or automatic exon primer determination procedure of the present invention, greatly speeds this design process, and with much more facility and flexibility.

Figure 9:
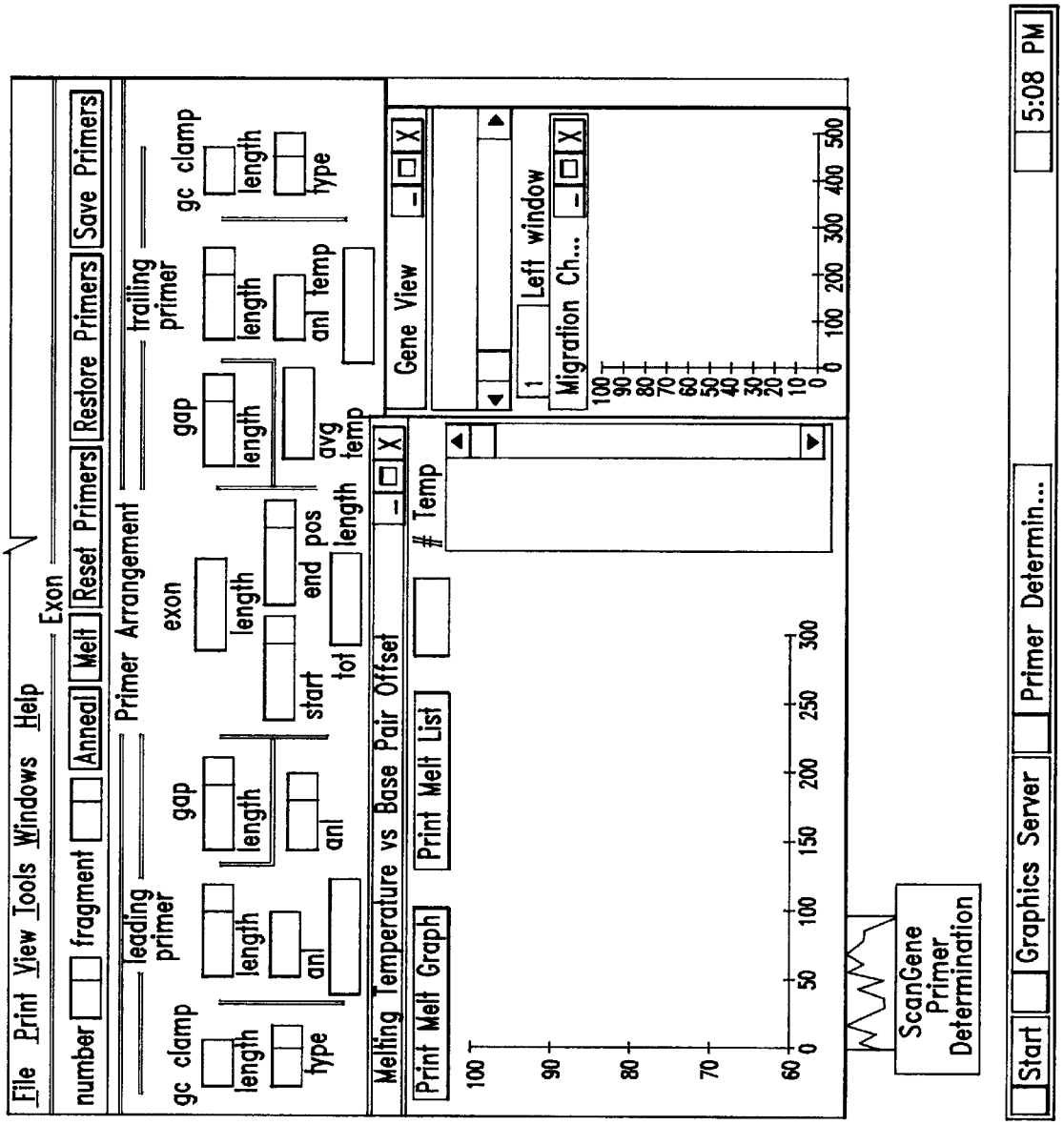
FIG. 9 shows a preferred computer display screen with the various monitoring and display icons, boxes or windows and options available to the investigator.

A semi-automatic version is shown in the microprocessor software implemented Flow Chart of FIGS. 7A and 7B, later described, controlling the computer display screen of FIGS. 9 to 14. The screen display format, as shown in FIG. 9, provides boxes or icons, such as "window" displays, an automatic plotting or graphing display region for simulated trial melting temperature profiles over all the gene fragments, and an automatically presented simulated 2-D gene fragment spot distribution presentation (2-D) of the type attainable by actual 2-D electrophoretic separation, as described in the said Vijg papers.

Description Of Display Screen

In the lower right of the screen is the 2-D pattern-distribution display area, labeled "Migration Ch," in which the melting temperature (in % UF) of the fragments is plotted as a function of the size of the fragments. The purpose of this migration chart/pattern is to insure that no two fragments will occupy the same place in the pattern, and thus mutations in all of the fragments will be detectable.

Above the Migration Ch area, under the title "Gene View", there is presented the window for displaying the sequence of the entire gene. The user can load the gene sequence into the program so that it is later possible to scroll through the gene in this window to locate the exons, as in capital letters, and the introns as in lower case letters. The Gene View makes it easy to locate the beginning and end of the exons and indicates to the user the total length of the fragment (i.e. exon, gaps, primers, and GC clamp).

On the left-hand lower and central portion of the screen, there is provided a "melting temperature vs. base pair offset" mapping area; and between this mapping area and the Migration Ch area, there is a tabular column space in which the individual melting temperatures Tm of each base pair is printed and scrollable.

In the upper center, boxes for indicating the selected number and fragment and the "exon length" are provided, defining the selected exon/fragment. The number the user enters here refers to the fragment for which the user is designing a test. Sometimes an exon is too long to analyze in a single fragment and thus must be divided into different fragments. For example, if exon 3 of a given gene needed to be divided into three fragments, the user would number the fragments 3.1, 3.2, and 3.3. These numbers would read exon 3 fragment 1, exon 3 fragment 2, and exon 3 fragment 3. To the left and right of this box, are windows or boxes labeled "gap", which are the boxes that tell the user the length of the gap between the end of the primer and the exon sequence. The box to the left indicates the gap between the end of the leading primer and the beginning of the exon, while the box to the right indicates the gap between the end of the exon and the beginning of the trailing primer sequence.

To the left and right of the gap-length boxes, are boxes labeled "leading primer" and "trailing primer", respectively. The numbers here represent the length of the primers, usually between 18 and 25 base pairs in length, as before described.

On the left and right of the primer boxes, there are also provided left and right boxes labeled "GC Clamp". The user can click on these boxes to select whether to place the GC clamp on the leading or trailing primer. Beneath the GC clamp box is the word "type", referring to the type of GC clamp that best suits a given fragment. The numbers 1, 2 and 3 are assigned to correspond to the earlier-described illustrative 30, 35 and 38 basepair clamps.

Below the primer boxes, are boxes "anl" for indicating the Tm of the primer sequences, which are referred to as the annealing temperatures of the primers. This function is especially useful in designing the before-described multiplex tests in which the annealing temperatures of the primers of the different fragments should optimally be within a few degrees of each other, as earlier stated.

Directly under these "anl" boxes, in turn, further boxes are provided in which the words "unique" or "not unique" appear. This refers to whether or not the given primer sequence occurs somewhere else in the gene. The function of this is to ensure that each amplicon has a set of primers which do not share sequence homology with any other 18–25 bp sequence, so that only the desired fragments will be amplified.

Figure 10:
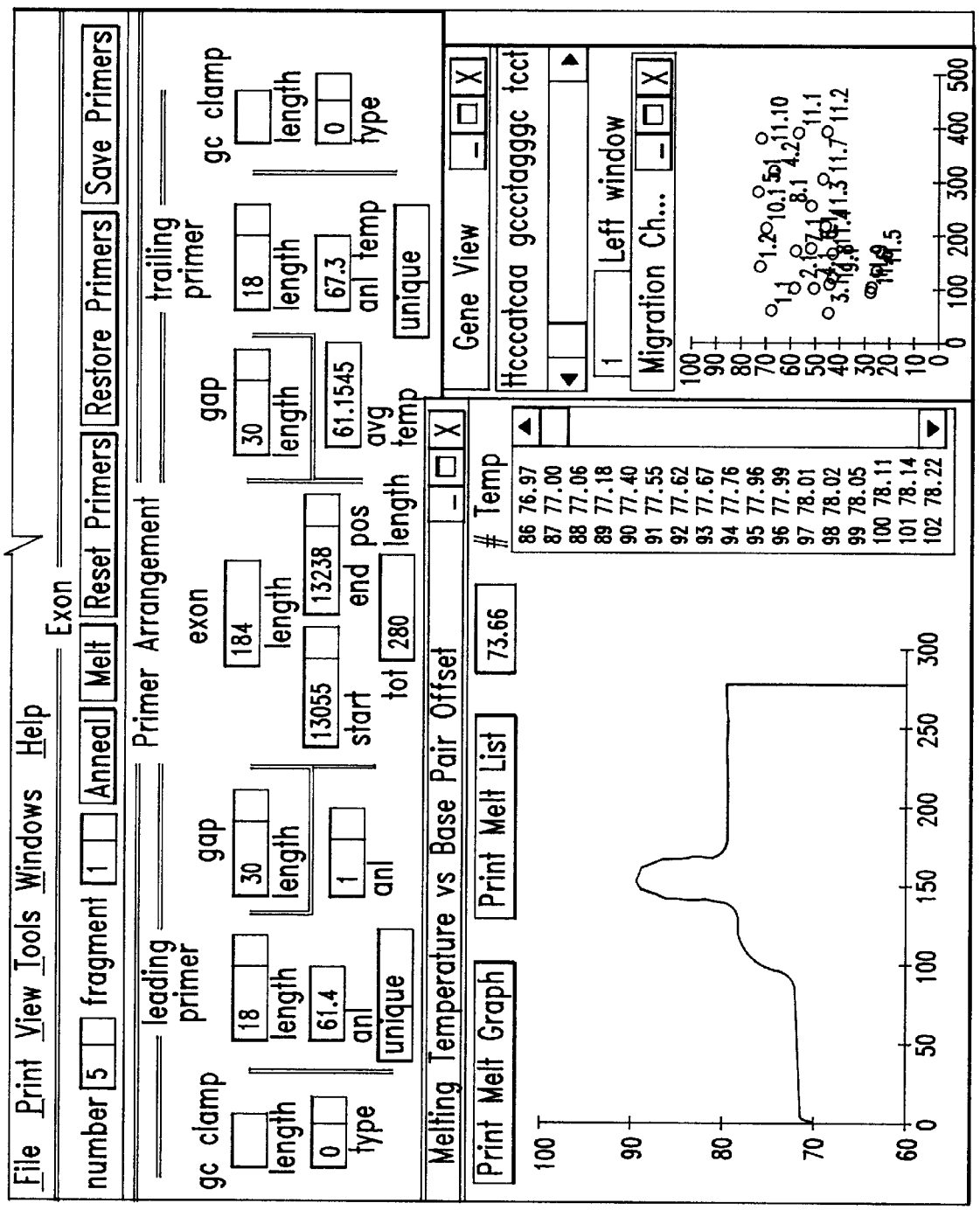
FIG. 10 shows this screen with inputs for a particular desired gene—in this illustration, P53 (SEQ. ID. No. X54156) involved in colon and other cancers, assuming no prior knowledge of appropriate primers, temperature gradients, etc.
Figure 11A:
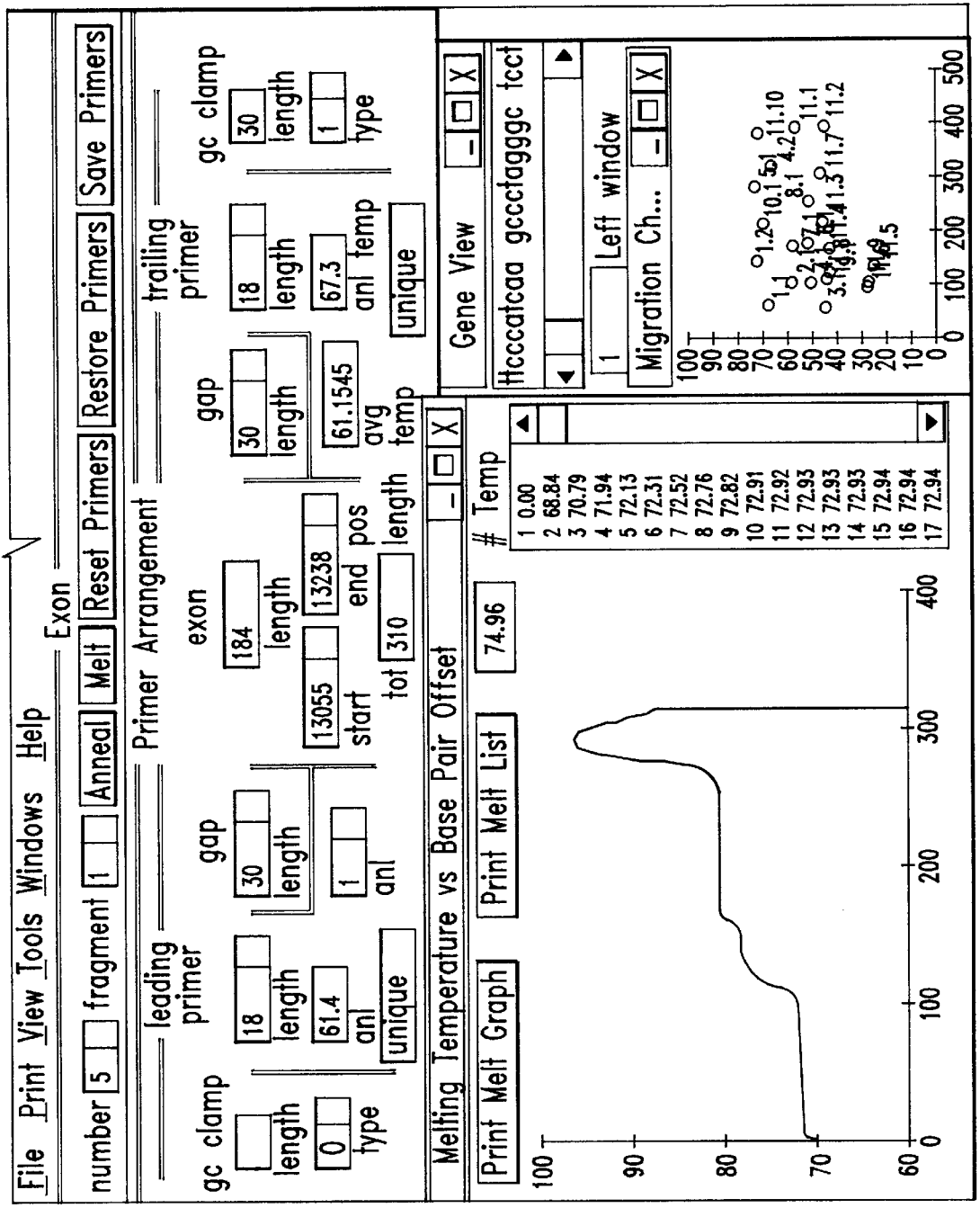
FIGS. 11A and 11B are similar views with different test values of primers, GC clamp, etc. producing unsatisfactory (simulated) melting profiles with multiple domains, FIG. 11A with the clamp located on the right, and FIG. 11B. on the left.
Figure 11B:
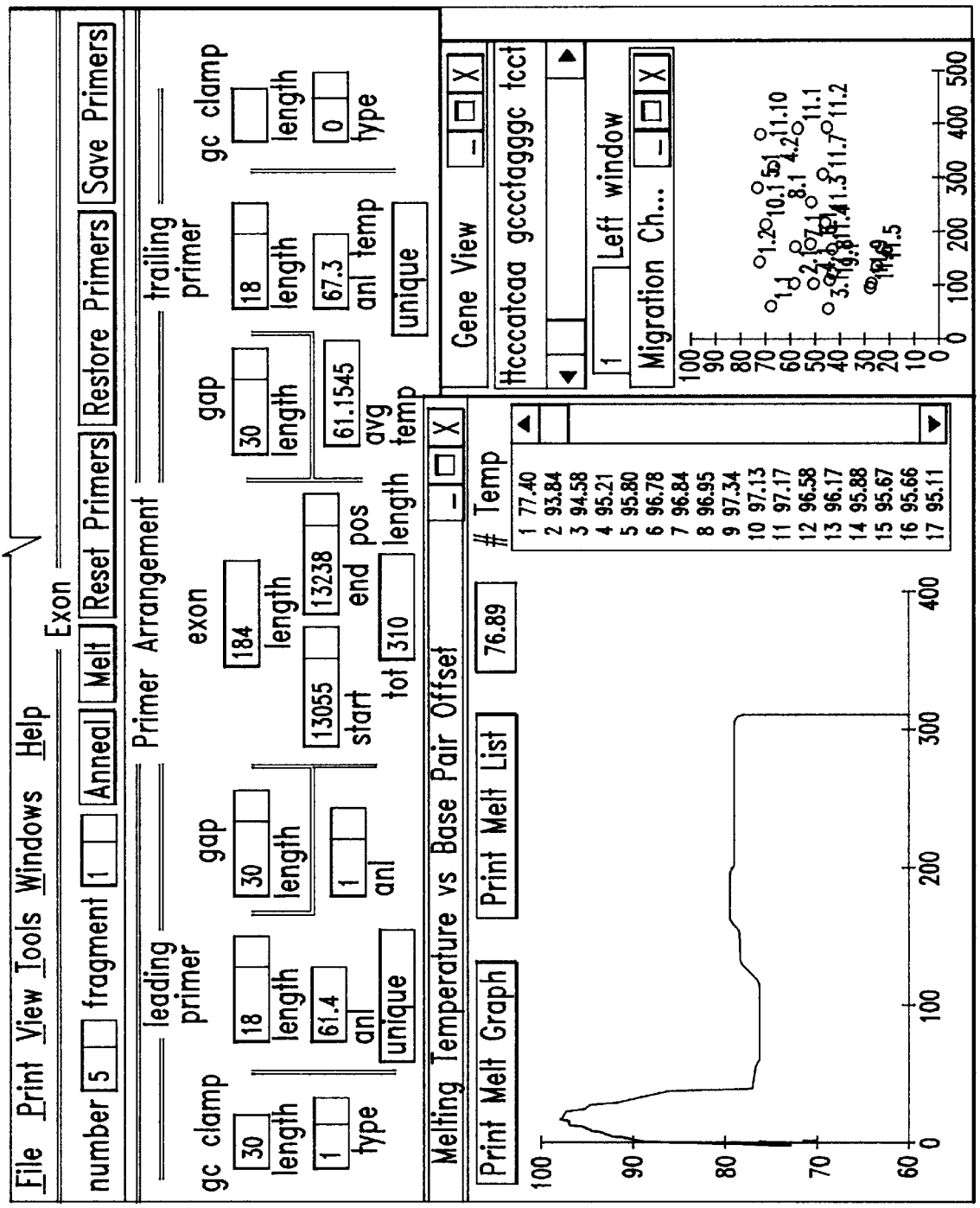
Figure 12:
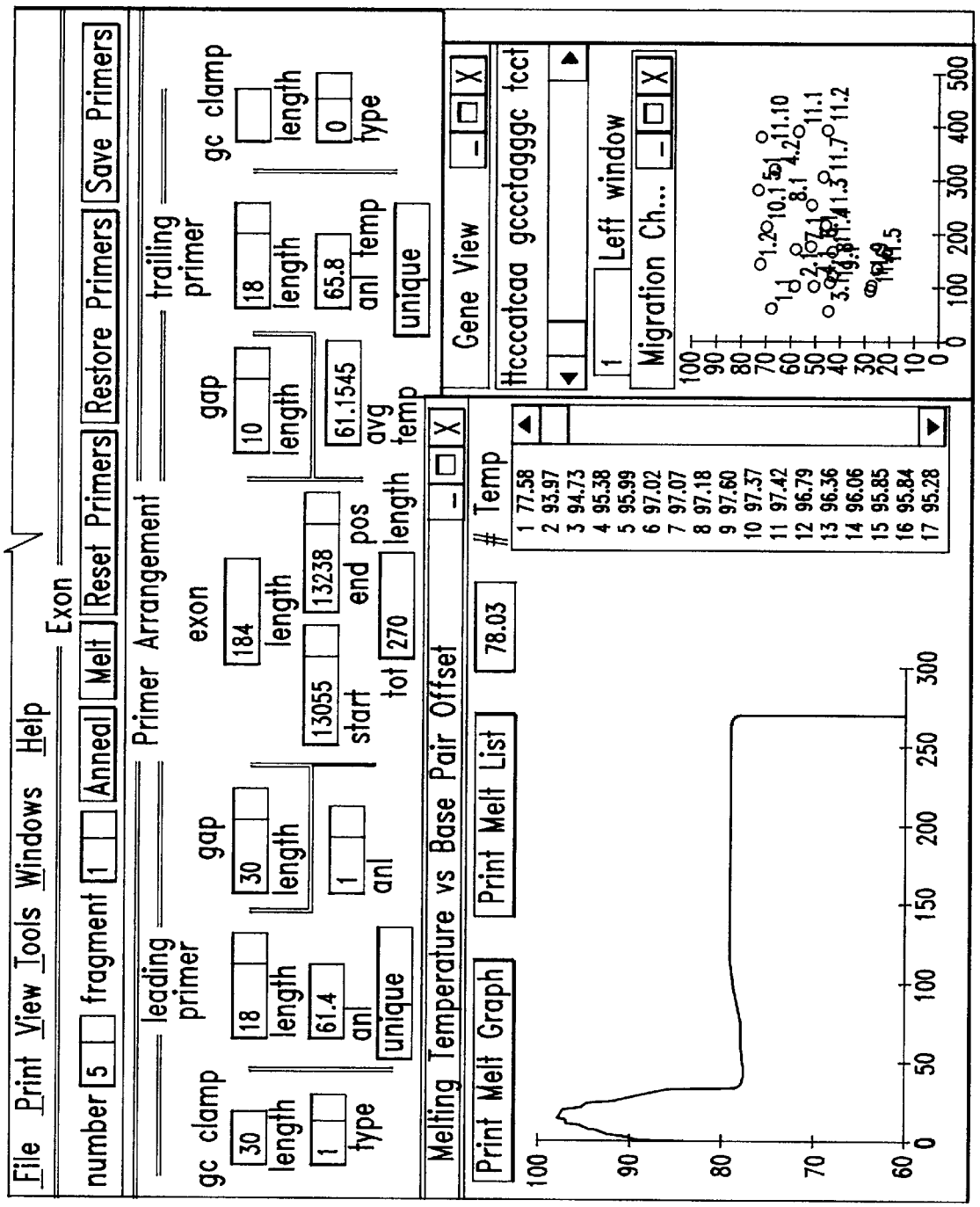
FIG. 12 shows a satisfactory melting profile for corrected test values of primer, GC clamp, etc., with FIGS. 11A, 11B and 12 showing variation of predicted melting curves of exons of the gene obtained with only slight variations in the positioning of one or more of PCR primers, lengths of primers and GC-clamp, type of GC-clamp, and length of the fragment, which serves to illustrate the real and qualitative features of the invention with respect to the final test design, and with FIG. 12 containing an additional column read-out of temperatures to the right of the graph.

The box that reads "Melt" at the top line of the display, when selected, commands the computer to calculate the Tm and construct a melting map of the fragment for the trial parameters which the user has indicated (primer lengths, etc.), FIGS. 10–12. If the melting map is optimal, as in FIG. 12, and the fragment occupies a unique location on the 2-D migration map, the user clicks on the box marked "Save Primers" at the top-line right. This will save all of the information concerning a given fragment; i.e. length of primers, gap length, GC clamp type and location. The information will be saved under whichever heading the user selected in the box designated the exon "fragment".

The box Reset Primers will reset the computer to the standard conditions of, for example, a 30 bp gap length and 18 bp primer length with no GC clamp.

"Restore Primers" recalls saved information concerning a given primer. The user types the exon fragment information in the exon fragment box and clicks on the Restore Primer box. If the user types in 3.2, for example, the computer will recall the primer positions, gap lengths, GC clamp location and type of exon 3, fragment 2.

Semi-Automatic Operation

Returning, now, to the semi-automatic version of operation in accordance with the invention, the operator inputs or controls, by a conventional "mouse" or the like, the sequencing of the program. The general procedure for the computer-aided design of optimized genetic screening tests based on such PCR/2-D electrophoresis (and including multiplex operation, as before discussed) is as follows:

Preliminary

1. Retrieve the gene sequence code (e.g., from Genbank). While the gene sequence code is a four-letter code (that is, a particular combination of A's, T's, C's and G's), the complete code that specifics a gene can be as long as 100,000 letters. Only small parts, however, each not more than 100–600 letters long, are considered important for making the test. These parts are the exons, and indications are given as to where they start and where they end in the total letter code. Small parts before and after each exon (splice sites) are also included as well as so-called regulatory regions close to the actual gene or some distance apart.

2. Find the exons in the letter code or specify other target fragments.

3. Position primers so as to surround the exons. Such primers, as before explained, are small parts of the letter code, i.e., about 20 letters, that define the boundaries of the exons to be tested. Primers should be completely outside the exon, from 5 letters outside it up to 100 letters outside.

Where required, as previously explained, it is allowed to split exons in two; that is, position four primers rather than two, so as to define an exon by two fragments rather than one (for very large exons even more fragments are allowed). In such case, however, the fragments must necessarily overlap by about 10 letters so as to assure that the exon is completely covered. At least one of the two primers defining a fragment should be coupled to a GC-clamp.

Melting Criterion

4. Run each fragment defined by its primers on a conventional melting profile generating program such as the before-mentioned Melt87 (or a derivative) program so as to generate melting curves. Each fragment starts with the first letter of its left primer and ends with the last letter of its right primer; so it includes the GC-clamp. Ideally, each melting curve, as previously explained, should consist of one high-melting domain (the GC-clamp) and one low-melting domain (the exon or part of it); and when this is not the case, the program should try other primer positions and/or split exons in half, and/or change the size of the GC-clamp, and/or add two, instead of one GC-clamp.

PCR Conditions

5. Compare the annealing temperature of the selected primers. They should be almost the same (at least the primers of one pair). The annealing temperatures of primers can be determined by using a conventional PCR-design program.

6. Compare the primer letter codes among each other and with the total letter code of the gene, so as to avoid overlap with any other than the defined fragments.

Two-Dimensional Distribution

7. Distribute the fragments defined by their primers over two dimensions; one dimension being the size (say, left to right) and the other dimension being the melting temperature (say, top to bottom) of the fragment. Avoid clustering, though some is unavoidable. The easiest way to separate clustered fragments is to change their size, which can be done by changing the position of the primers and/or changing the size of the GC-clamp (a 5–10-letter change is usually enough to separate fragments of the same size). Select a gradient of increasing melting temperature so as to allow an optimal spread of the fragments from top to bottom of the gel.

RBI Example

As a first example, the above steps will now be schematically translated into the scheme, programmed under "Windows", for the before-mentioned tumor-suppresser gene RB1, a large gene, and with a test design that requires extensive optimization. Like many other genes, the sequence of this gene is available in Genbank from which it may be retrieved and copied into a file to be subjected to the procedure representing the invention. First, the start and endpoints of the exons or coding sequences of this gene are indicated by typing in the respective sequences until the program indicates uniqueness on the display. Then, the system starts by assuming 18-mer primer, gaps between primers, and exons of 30 bp and a defined GC-clamp of 30 bp long. A melting profile of this configuration as well as the PCR annealing temperatures of the primers is automatically obtained. Either by observation of the screen or automatic monitoring; a decision is taken about the suitability of the melting curve. If not entirely satisfactory. one or more of the following parameters are varied: gap-size, primer-size, GC-clamp, until a satisfactory profile and set of annealing temperatures is obtained. If this proves to be impossible, the fragment is split in two or more fragments until optimal melting behavior is attained.

Figure 7A:
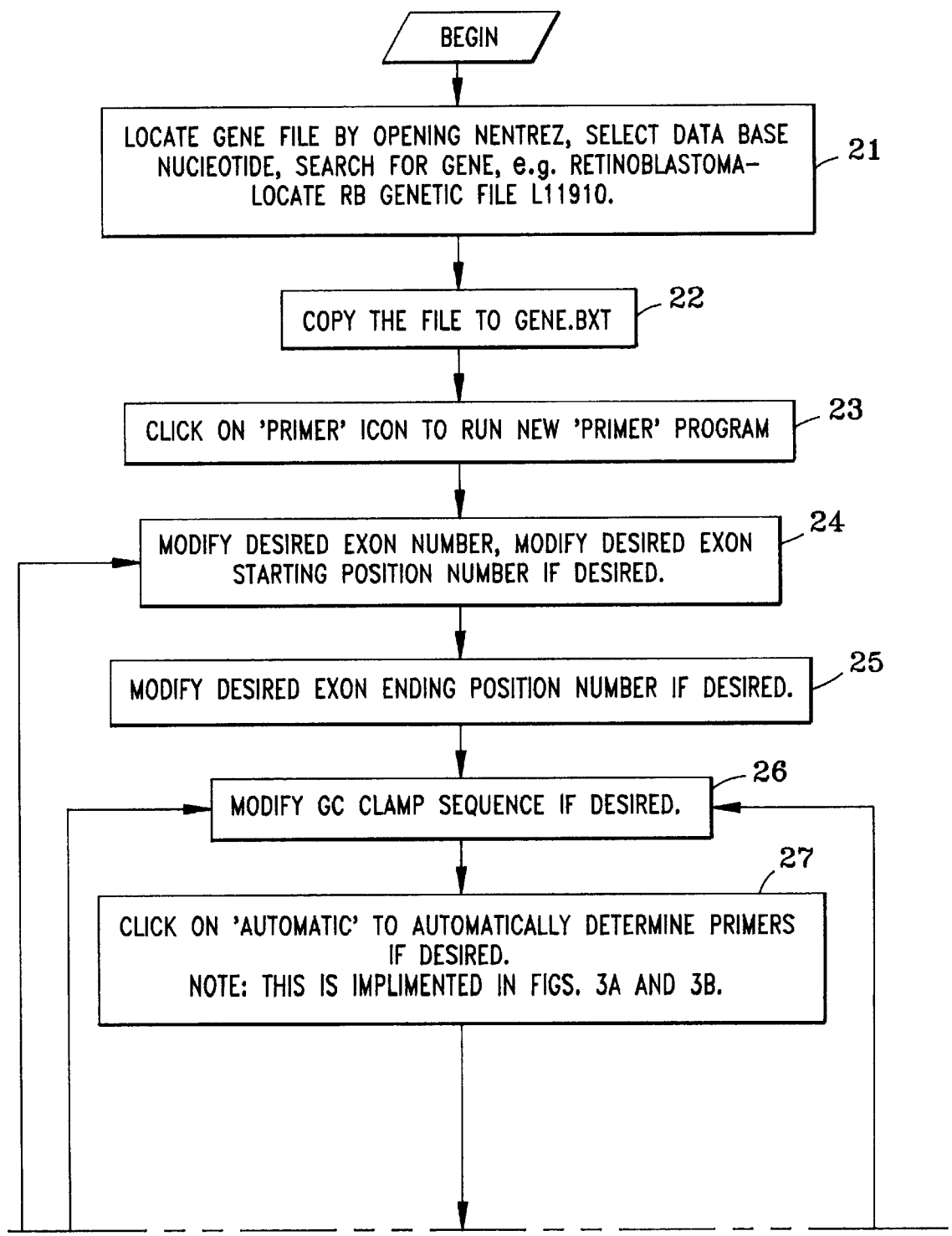
FIGS. 7A and 7B are similar flow charts of the steps involved in semi-automatically with operator assist, rapidly designing appropriate test primers, GC clamps and melting profiles and providing simulated electrophoretic gene separation displays in accordance with the computer-aided software techniques of the present invention.
Figure 7B:
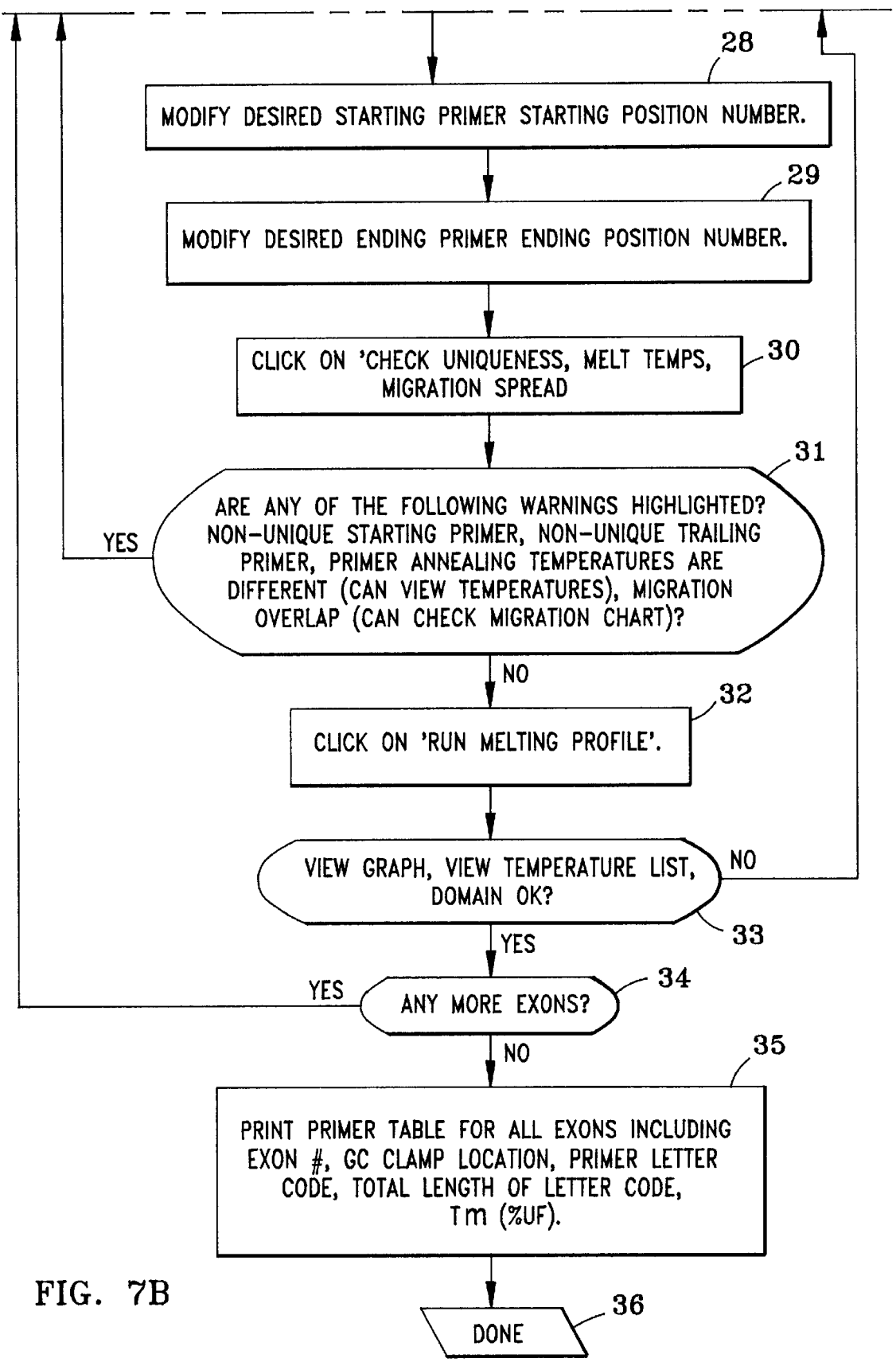

Referring more specifically to the previously mentioned Flow Chart of FIGS. 7A and 7B, the illustrative RB gene is located (21) and file copied (22). The primer window, FIG. 9, is activated (23), injecting a trial primer letter sequence. The trial GC sequence is modified at (26), if required. Automatic monitoring can cause variation of the primer start and end positions as required (28, 29) and doing so while monitoring uniqueness (30), melting temperature mapping, and display separation at Migration Ch, FIG. 9.

If proper trial values are available, the melting profile generation is checked (32), and the graph viewed (33) to insure a satisfactory single domain over the gene fragments. If there are no more exons (34), the resulting primer table for all exons, including their exon numbers, GC clamp locations, proper letter codes, total length of letter code, and Tm values are reported by print-out (35), completing the test design (36).

In the event, however, that a warning is highlighted (31) of any of non-unique starting and/or trailing primers, primer annealing temperatures, or spot migration crowding or overlap, and/or in the event more exons are present (34), repetition of variation of exon numbers and starting an ending positions (24) and (25), and GC clamp sequences (26) is effected to provide proper values or conditions with automatic primer determination at (27) as later explained.

Automatic Version

Figure 8A:
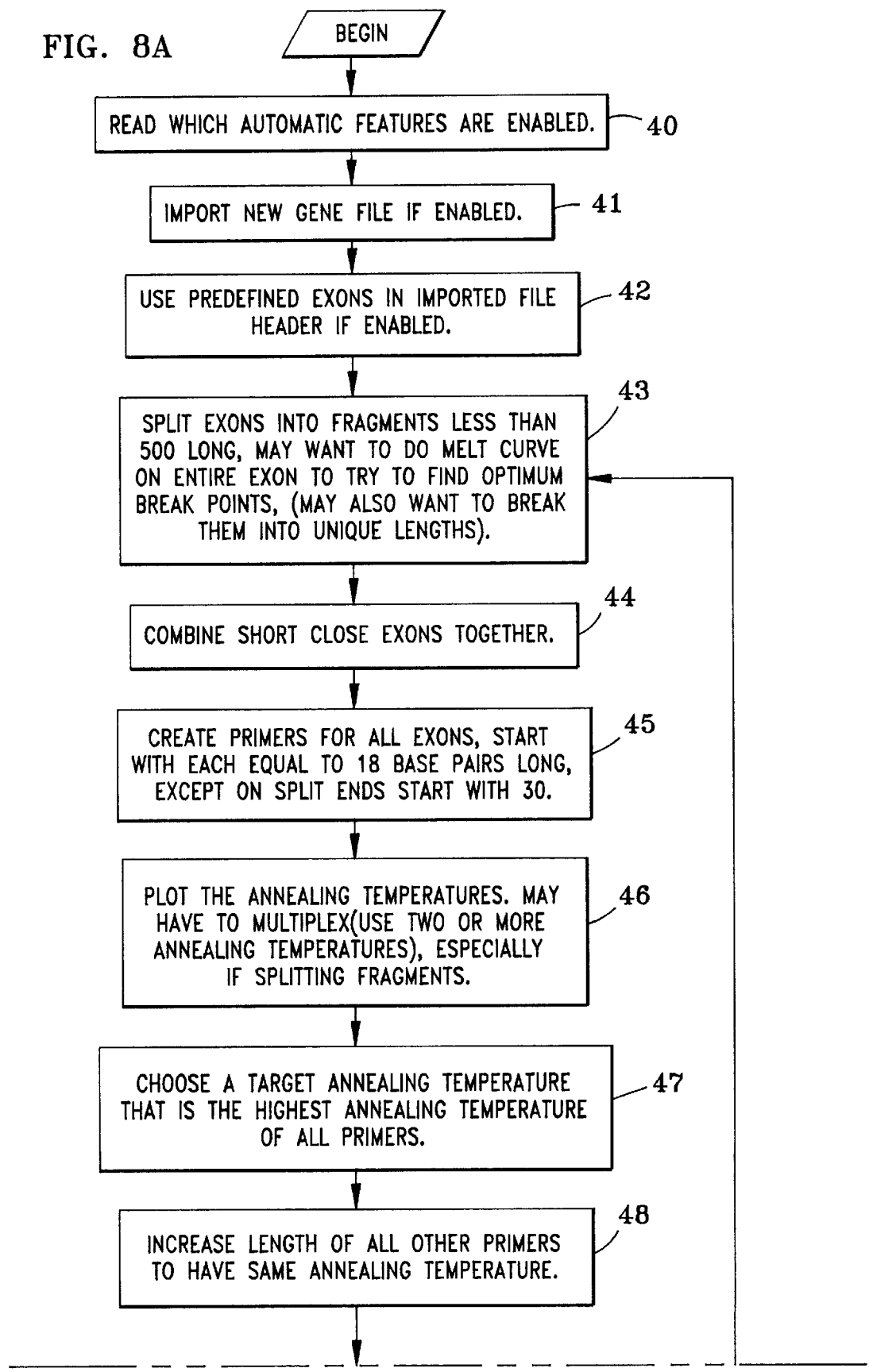
FIGS. 8A and 8B are flow charts similar to FIGS. 6A and 6B for full automation.
Figure 8B:
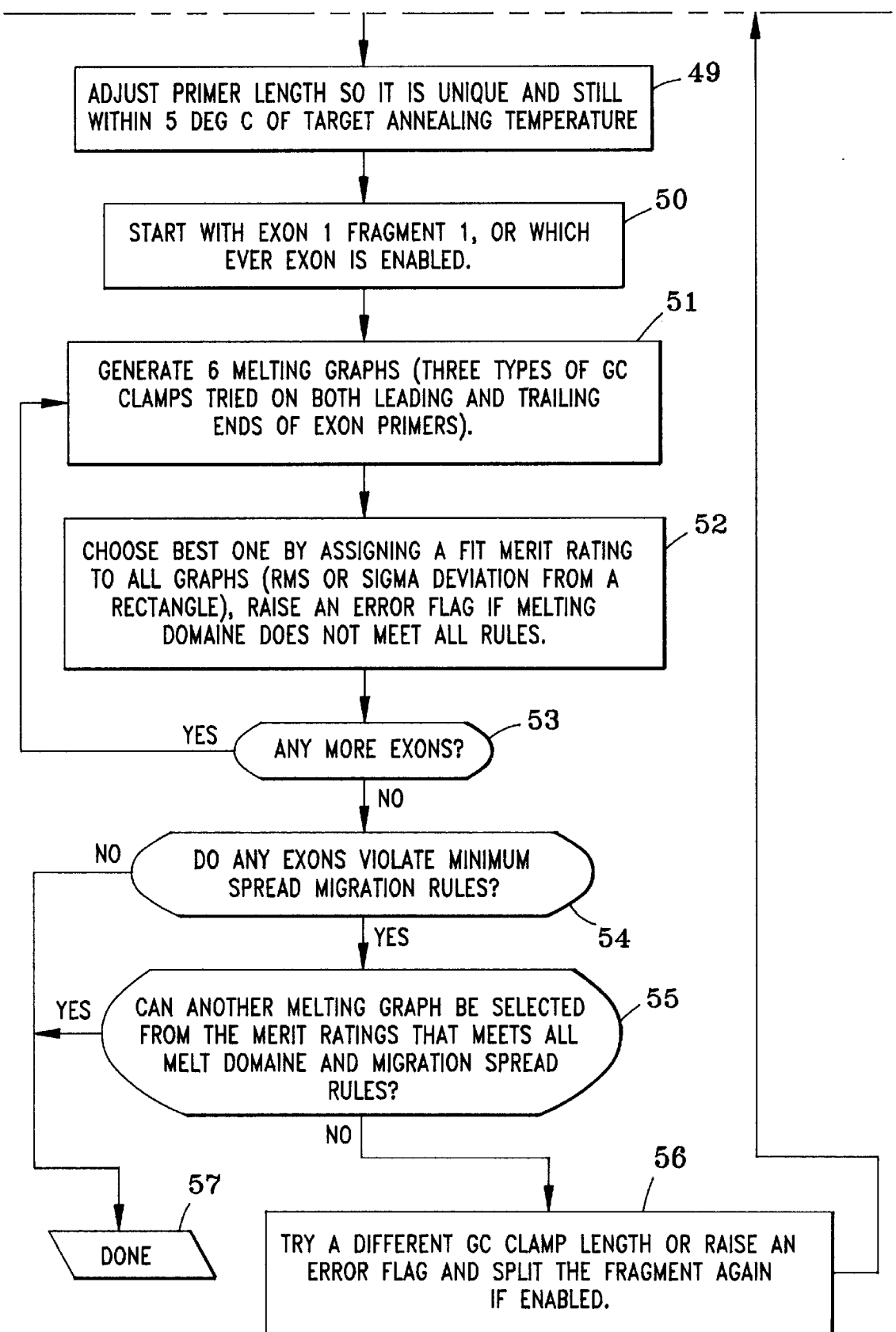

For fully automatic test design where the setting of trial values is effected by known types of feedback control in response to deviation from rules for a standard single domain melting profile, for example, predisposed exons are imported in the file header when enabled (42), FIG. 8A, after automatic features (40) and the gene file (41) have been established. As previously discussed, fragments less than, say, 500 long are selected (43), and short close exons are combined (44). If desired, optimum break points on the melting curve of the entire gene may be located and/or unique lengths of fragments selected. Trial primers are then inputted for all exons (45) which, from experience, preferably start, for example, with each equal to 18 base pairs long, and with 30 base pair lengths for split ends. The annealing temperatures are then plotted (46) with selection (47) of the highest values, and the increase of all other primer lengths to achieve substantially the same annealing temperature (48). As before described, the primer lengths are adjusted (49), FIG. 8B, for uniqueness, consistent with substantially common annealing temperatures—say, for example, within 5° C. of one another.

Starting with a first exon fragment (50), a pre-set number (such as six) trial melting graphs are run for three types of trial GC clamps (51), and the closest fit to the desired standard single domain profile shape (52) is selected (53), with the fit being measured. for example, by one of RMs or sigma deviation from a rectangle. If the profile design rules are not met, an error flag is raised or highlighted. For additional exons (53), steps (51) and (52) are repeated. If the exons meet minimum display spread migration rules at migration Ch, FIG. 9, the design is complete (57). If, however, any exons violate minimum display spread migration rules (54), it is determined whether another melting profile can be selected to meet the required domain and spot migration spread rules (55); and, if not, different GC clamp lengths are tried or an error flag again raised (56).

P. 53 Gene Example

In the successive displays of FIGS. 10–14, another example is presented of the carrying out of the procedures of the invention for another impairment gene—the P53 gene.

Starting with a number 5, fragment 1, FIG. 10, for a gene sequence SEQ. ID. No. 1, below ("gene view" box), trial values of exon length 184, gaps 30 leading and trailing primer lengths 18, and annealing temperature of 67.3, and no GC clamp, the multi-domain unsatisfactory melting temperature profile was produced at the lower left. Adding a right-hand GC clamp of 30, FIG. 11A, did not adequately improve the melting profile. Substituting a 30 GC clamp at the left provided some improvement in reducing the multiple domain excursions, FIG. 11B. Reducing the gap length to 10, FIG. 12, however, provided a satisfactory flat domain following the GC clamp left-hand peak.

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: double stranded
      (D) TOPOLOGY: linear (ii) MOLECULE TYPE: genomic DNA (iii) HYPOTHETICAL: no (iv) ANTI-SENSE: no (vi) ORIGINAL SOURCE:
      (A) ORGANISM: human (vii) IMMEDIATE SOURCE:
      (A) LIBRARY: genomic (viii) POSITION IN GENOME:
      (A) CHROMOSOME/SEGMENT: 17/p (xi) SEQUENCE DESCRIPTION: SEQ ID NO: 1:

TTCCCATCAA GCCCTAGGGC TCCT      24

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: double stranded
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (vii) IMMEDIATE SOURCE:
        (A) LIBRARY: genomic (viii) POSITION IN GENOME:
        (A) CHROMOSOME/SEGMENT: 17/p (xi) SEQUENCE DESCRIPTION: SEQ ID NO: 2:

CCTCCCATGT GCTCAAGA                                            18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: double stranded
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (vii) IMMEDIATE SOURCE:
        (A) LIBRARY: genomic (viii) POSITION IN GENOME:
        (A) CHROMOSOME/SEGMENT: 17/p (xi) SEQUENCE DESCRIPTION: SEQ ID NO: 3:

AAAGCACGCT CCCAGCCC                                            18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: double stranded
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (vii) IMMEDIATE SOURCE:
        (A) LIBRARY: genomic (viii) POSITION IN GENOME:
        (A) CHROMOSOME/SEGMENT: 17/p

```
            (xi) SEQUENCE DESCRIPTION: SEQ ID NO: 4:

CACCGTCCAG GGAGCAGG                                                                18

(2) INFORMATION FOR SEQ ID NO:5:

(i) SEQUENCE CHARACTERISTICS:
         (A) LENGTH: 18 base pairs
         (B) TYPE: nucleic acid
         (C) STRANDEDNESS: double stranded
         (D) TOPOLOGY: linear (ii) MOLECULE TYPE: genomic DNA (iii) HYPOTHETICAL: no (iv) ANTI-SENSE: no (vi) ORIGINAL SOURCE:
         (A) ORGANISM: human (vii) IMMEDIATE SOURCE:
         (A) LIBRARY: genomic (viii) POSITION IN GENOME:
         (A) CHROMOSOME/SEGMENT: 17/p (xi) SEQUENCE DESCRIPTION: SEQ ID NO: 5:

GAGAGCCCGT GACTCAGA                                                                18

(2) INFORMATION FOR SEQ ID NO:6:

(i) SEQUENCE CHARACTERISTICS:
         (A) LENGTH: 18 base pairs
         (B) TYPE: nucleic acid
         (C) STRANDEDNESS: double stranded
         (D) TOPOLOGY: linear (ii) MOLECULE TYPE: genomic DNA (iii) HYPOTHETICAL: no (iv) ANTI-SENSE: no (vi) ORIGINAL SOURCE:
         (A) ORGANISM: human (vii) IMMEDIATE SOURCE:
         (A) LIBRARY: genomic (viii) POSITION IN GENOME:
         (A) CHROMOSOME/SEGMENT: 17/p (xi) SEQUENCE DESCRIPTION: SEQ ID NO: 6:

AAGCGTCTCA TGCTGGAT                                                                18

(2) INFORMATION FOR SEQ ID NO:7:

(i) SEQUENCE CHARACTERISTICS:
         (A) LENGTH: 18 base pairs
         (B) TYPE: nucleic acid
         (C) STRANDEDNESS: double stranded
         (D) TOPOLOGY: linear (ii) MOLECULE TYPE: genomic DNA (iii) HYPOTHETICAL: no (iv) ANTI-SENSE: no (vi) ORIGINAL SOURCE:
         (A) ORGANISM: human (vii) IMMEDIATE SOURCE:
         (A) LIBRARY: genomic
```

(viii) POSITION IN GENOME:
              (A) CHROMOSOME/SEGMENT: 17/p (xi) SEQUENCE DESCRIPTION: SEQ ID NO: 7:

GCCCTTCCAA TGGATCCA                                                         18

(2) INFORMATION FOR SEQ ID NO:8:

(i) SEQUENCE CHARACTERISTICS:
              (A) LENGTH: 18 base pairs
              (B) TYPE: nucleic acid
              (C) STRANDEDNESS: double stranded
              (D) TOPOLOGY: linear (ii) MOLECULE TYPE: genomic DNA (iii) HYPOTHETICAL: no (iv) ANTI-SENSE: no (vi) ORIGINAL SOURCE:
              (A) ORGANISM: human (vii) IMMEDIATE SOURCE:
              (A) LIBRARY: genomic (viii) POSITION IN GENOME:
              (A) CHROMOSOME/SEGMENT: 17/p (xi) SEQUENCE DESCRIPTION: SEQ ID NO: 8:

GAAGCGAAAA TTCATGGG                                                         18

(2) INFORMATION FOR SEQ ID NO:9:

(i) SEQUENCE CHARACTERISTICS:
              (A) LENGTH: 18 base pairs
              (B) TYPE: nucleic acid
              (C) STRANDEDNESS: double stranded
              (D) TOPOLOGY: linear (ii) MOLECULE TYPE: genomic DNA (iii) HYPOTHETICAL: no (iv) ANTI-SENSE: no (vi) ORIGINAL SOURCE:
              (A) ORGANISM: human (vii) IMMEDIATE SOURCE:
              (A) LIBRARY: genomic (viii) POSITION IN GENOME:
              (A) CHROMOSOME/SEGMENT: 17/p (xi) SEQUENCE DESCRIPTION: SEQ ID NO: 9:

TCCCAGCCCA ACCCTTGT                                                         18

(2) INFORMATION FOR SEQ ID NO:10:

(i) SEQUENCE CHARACTERISTICS:
              (A) LENGTH: 18 base pairs
              (B) TYPE: nucleic acid
              (C) STRANDEDNESS: double stranded
              (D) TOPOLOGY: linear (ii) MOLECULE TYPE: genomic DNA (iii) HYPOTHETICAL: no (iv) ANTI-SENSE: no (vi) ORIGINAL SOURCE:

(A) ORGANISM: human (vii) IMMEDIATE SOURCE:
            (A) LIBRARY: genomic (viii) POSITION IN GENOME:
            (A) CHROMOSOME/SEGMENT: 17/p (xi) SEQUENCE DESCRIPTION: SEQ ID NO: 10:

GGGGGCTGAG GACCTGGT                                                  18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: double stranded
            (D) TOPOLOGY: linear (ii) MOLECULE TYPE: genomic DNA (iii) HYPOTHETICAL: no (iv) ANTI-SENSE: no (vi) ORIGINAL SOURCE:
            (A) ORGANISM: human (vii) IMMEDIATE SOURCE:
            (A) LIBRARY: genomic (viii) POSITION IN GENOME:
            (A) CHROMOSOME/SEGMENT: 17/p (xi) SEQUENCE DESCRIPTION: SEQ ID NO: 11:

GGGGAGCAGC CTCTGGCA                                                  18

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: double stranded
            (D) TOPOLOGY: linear (ii) MOLECULE TYPE: genomic DNA (iii) HYPOTHETICAL: no (iv) ANTI-SENSE: no (vi) ORIGINAL SOURCE:
            (A) ORGANISM: human (vii) IMMEDIATE SOURCE:
            (A) LIBRARY: genomic (viii) POSITION IN GENOME:
            (A) CHROMOSOME/SEGMENT: 17/p (xi) SEQUENCE DESCRIPTION: SEQ ID NO: 12:

AAGACCCAGG TCCAGATG                                                  18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: double stranded
            (D) TOPOLOGY: linear (ii) MOLECULE TYPE: genomic DNA (iii) HYPOTHETICAL: no

```
      (iv) ANTI-SENSE: no (vi) ORIGINAL SOURCE:
           (A) ORGANISM: human (vii) IMMEDIATE SOURCE:
           (A) LIBRARY: genomic (viii) POSITION IN GENOME:
           (A) CHROMOSOME/SEGMENT: 17/p (xi) SEQUENCE DESCRIPTION: SEQ ID NO: 13:

GGCCAGGCAT TGAAGTCT                                                    18

(2) INFORMATION FOR SEQ ID NO:14:

(i) SEQUENCE CHARACTERISTICS:
           (A) LENGTH: 18 base pairs
           (B) TYPE: nucleic acid
           (C) STRANDEDNESS: double stranded
           (D) TOPOLOGY: linear (ii) MOLECULE TYPE: genomic DNA (iii) HYPOTHETICAL: no (iv) ANTI-SENSE: no (vi) ORIGINAL SOURCE:
           (A) ORGANISM: human (vii) IMMEDIATE SOURCE:
           (A) LIBRARY: genomic (viii) POSITION IN GENOME:
           (A) CHROMOSOME/SEGMENT: 17/p (xi) SEQUENCE DESCRIPTION: SEQ ID NO: 14:

CAACTCTGTC TCCTTCCT                                                    18

(2) INFORMATION FOR SEQ ID NO:15:

(i) SEQUENCE CHARACTERISTICS:
           (A) LENGTH: 18 base pairs
           (B) TYPE: nucleic acid
           (C) STRANDEDNESS: double stranded
           (D) TOPOLOGY: linear (ii) MOLECULE TYPE: genomic DNA (iii) HYPOTHETICAL: no (iv) ANTI-SENSE: no (vi) ORIGINAL SOURCE:
           (A) ORGANISM: human (vii) IMMEDIATE SOURCE:
           (A) LIBRARY: genomic (viii) POSITION IN GENOME:
           (A) CHROMOSOME/SEGMENT: 17/p (xi) SEQUENCE DESCRIPTION: SEQ ID NO: 15:

TGTCGTCTCT CCAGCCCC                                                    18
```

Figure 13:
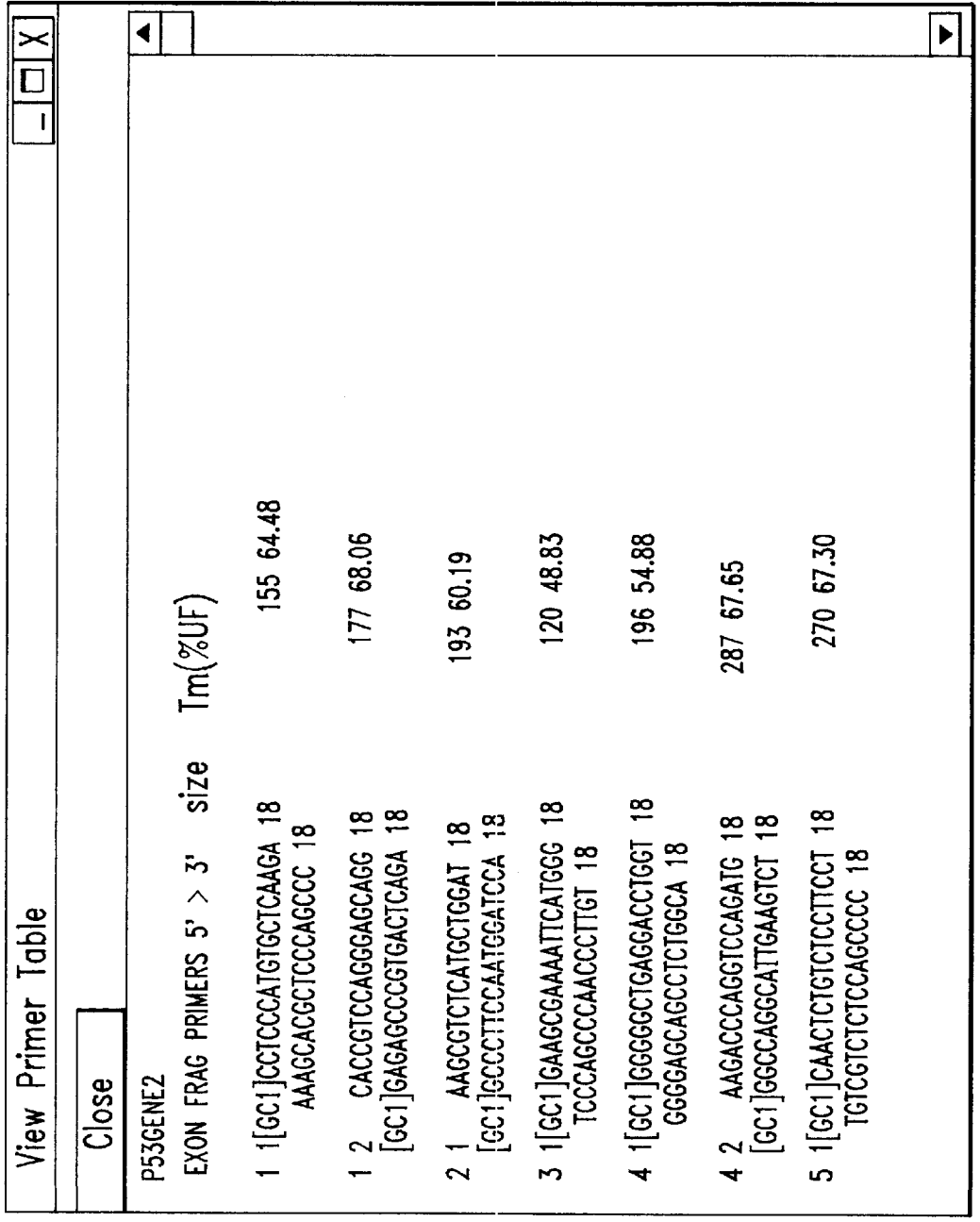
FIG. 13 illustrates displays of sequences with melting temperature.
Figure 14:
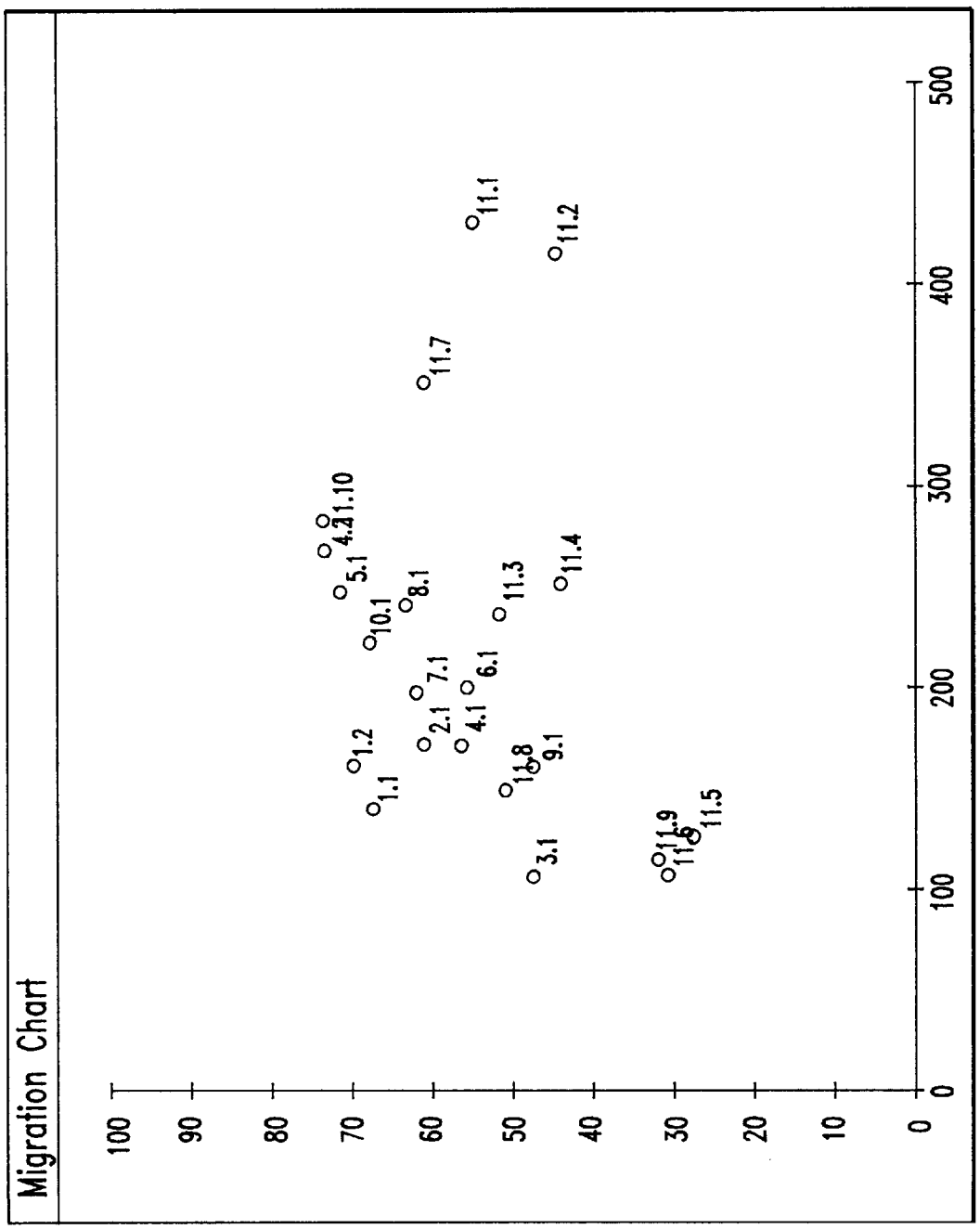
FIG. 14 shows a predicted 2-D display that the design of the invention will enable to be produced in actual 2-D electrophoresis operation in accordance with the design.

As before described, tables of primer sequences are displayable with predicted average melting temperature as an expanded View Primer Table, FIG. 13 (SEQ. ID. Nos. 2–15 below); and the design-predicted resulting 2-D electrophoretic fragment spot "Migration Ch" chart may be displayed and enlarged as in FIG. 14.

Other arrangements of display boxes and presentations are, of course, possible with the same general underlying

What is claimed is:

1. A computer-assisted method for generating a design simulation of comprehensive genetic DNA diagnostic tests using PCR methodology and the separation of PCR fragments by 2D electrophesis for screening mutations in genes for use in actual PCR and 2D electrophoresis tests, that comprises, inputting a computer microprocessor with a desired exon fragment ATGC letter sequence; programming the microprocessor first set to select a trial start and end of the sequence; then, selecting and positioning a pair of trial primer letter sequences forming the opposite boundaries of the exon fragments to be tested; adding a trial letter sequence of GC clamp to at least one primer; generating trial melting profiles for the primers and GC clamps, to determine whether the profile consists of a GC clamp peak melting value and a substantially single flat domain of lower melting value for the fragment; and in the event that the trial profile has multiple and not a substantially single flat domain, selecting other trial primer letter sequences and GC clamp letter sequence lengths and generating said profiles therefrom until such a substantially single flat domain is attained, determining annealing temperatures for the primers and comparing the annealing temperatures to select primers having substantially similar annealing temperatures for PCR annealing; comparing the primer letter sequences with other known gene sequences to insure the uniqueness of and to avoid overlap with other than the desired exon fragment; simulating a 2D distribution of the desired exon fragment by separation of PCR fragments along one dimension by size and along an orthogonal dimension by melting temperature; selecting a gradient of increasing melting temperatures along the orthogonal dimension to allow spread of the PCR fragments therealong; reporting the design simulation selected primer sets and temperature gradient for actual PCR and 2D electrophoresis tests; providing a sample of a gene fragment corresponding to the desired gene fragment of the simulation; and using the reported selected design simulation primer sets and temperature gradient in PCR and 2D electrophorsis operations on said sample; and performing PCR and 2D electrophoresis operations on said sample, using the reported selected design simulation primer sets and temperature gradient.

2. A method as claimed in claim 1 and in which, in the event of overlap clustering of the PCR fragments along the one dimension, changing the position of primers and/or changing the size of the GC clamp sequences to separate PCR fragments of similar length.

3. A method as claimed in claim 1 and in which the sequence of genes is obtained from a data base and, during said design generating is copied into a file for use in carrying out said method.

4. A method as claimed in claim 1 and in which, in the event a trail melting profile is obtained that does not have a substantially single domain, one or more of primer letter sequence and GC clamp letter sequence length is varied until a desired profile and set of annealing temperatures is obtained.

5. A method as claimed in claim 4 and in which the varying of the length of the GC clamp letter sequence is effected by adding a second GC clamp letter sequence.

6. A method as claimed in claim 1 and in which the annealing temperatures of the primers are determined by a predetermined PCR primer program.

7. A method as claimed in claim 1 and in which, if a desired melting profile is not obtained, the exon fragment sequence is split into parts inputted into the microprocessor with trial start and ends of the sequences determined for each part.

8. A method as claimed in claim 7 and in which the exon fragment letter sequence is split in two with two pairs of primers parts, each with some letter overlap.

9. A method as claimed in claim 1 and in which the pair of primer letter sequences that form the boundaries of the exon fragment to be tested are small compared with the exon fragment letter sequence.

10. A method as claimed in claim 9 and in which the primer letter sequences are about 20 letters.

11. A method as claimed in claim 9 and in which the primers are positioned from about 5 to up to about 100 letters outside the exon letter sequences.

12. A method as claimed in claim 1 and in which the melting profile is displayed to a monitoring operator on a computer display screen, and the selecting of the exon fragment letter sequences, primer letter sequences and GC clamp letter sequences are manually entered by the operator and displayed on the screen.

13. A method as claimed in claim 1 and in which the melting profile is automatically monitored, and start and end exon fragment letter sequence, primer letter sequence and GC clamp sequence are automatically varied as required until a predetermined single domain melting profile is attained.

14. A method as claimed in claim 1 and in which the fragment distribution is displayed on a computer display screen.

15. A method as claimed in claim 14 and in which, upon an operator monitoring the computer display screen and noting fragment overlap clustering, the operator enters programming variations in one or more of the position of the primers and the length of the GC clamp letter sequences to separate the fragments on the screen.

16. A method as claimed in claim 14 and in which the fragment distribution is automatically monitored, and upon detection of fragment clustering, varying the programming of one or more of the position of the primers and the length of the GC clamp sequence to separate the fragments.

17. A method as claimed in claim 1 and in which the temperature gradient distribution is displayed upon a computer display screen.

18. A method as claimed in claim 1 and in which PCR operation is carried out upon a sample comprising a gene having exon fragments of the same desired exon fragment sequence as the design simulation, and 2D electrophoresis is then carried out, using the reported den simulation primer sets and temperature gradient.

19. A method as claimed in claim 18 and in which the PCR operation is carried out after adding primer pairs to groups of the gene exons by effecting long-distance PCR amplifications thereof in a common tube or vessel to achieve long resulting amplicons; then adding further primer pairs to each of the amplicons and effecting multiplex PCR amplifications thereof in the common tube or vessel with relatively short resulting amplicons; and then 2-D electrophoretically separating the amplications.

20. A method as claimed in claim 1 and in which the reporting comprises display upon a computer display screen, under the control of the programmed microprocessor, of:

a) the trial profiles of the melting temperature for the gene fragments;

b) 2-D maps of the melted fragments;

c) a table of the primer sequences;

d) readout of the annealing temperatures of all the primers; and e) the primer-gene sequence; alignments.

21. A method as claimed in claim 20 and in which the melting temperature is presented as a percentage of ureaformamide.

22. A computer-assisted method for generating the design of genetic DNA diagnostic tests using PCR methodology and 2D electrophoresis for screening for mutations in genes and for use in actual PCR and 2D electrophoresis tests, that comprises, programming a computer microprocessor to input a desired gene exon fragment ATCG letter sequence; indicating the start and end of the desired sequence, primer letter sequence sets forming the boundaries of the exon fragment, and GC clamp letter sequences therefor; generating simulated conditions for PCR primer annealing; generating 2-D electrophoresis fragment separation simulation including a simulated melting profile of the fragments by varying fragment letter sequence size, GC clamp letter sequence size and primer letter sequence size to achieve a single domain profile of predetermined melting temperature for the gene exon fragment, clamped by a melting temperature high compared to the predetermined melting temperature for the GC clamp letter sequence; reporting the selected primer sets; providing a sample of gene fragment corresponding to the desired gene exon fragment and using the reported selected primer sets for testing said sample; and performing PCR and 2D electrophoresis operations on said sample, using the reported selected design simulation primer sets and temperature gradient.

23. A method as claimed in claim 22 and in which the reporting comprises displaying said primer sets and GC clamp letter sequences, melting temperature values and fragment size and melting temperature profile on a computer display screen.

24. A method as claimed in claim 23 and in which all the letter sequences and said values are displayed in window or shape type displays.

25. A method as claimed in claim 23 and in which all the letter sequence sizes are varied by an operator viewing the same in window or box shape displays on the display screen.

26. A method as claimed in claim 22 and in which the said varying is effected automatically in response to an inputted pre-set melting temperature gradient.

27. Computer-aiding apparatus for generating the design of comprehensive genetic DNA diagnostic tests using on PCR and 2-D electrophoresis operations for screening for mutations in genes, having, a computer microprocessor being software-programmed to effect the steps of method claim 1.

* * * * *